(12) United States Patent
Weeks et al.

(10) Patent No.: US 9,198,829 B2
(45) Date of Patent: *Dec. 1, 2015

(54) DELAMINATION RESISTANT PHARMACEUTICAL GLASS CONTAINERS CONTAINING ACTIVE PHARMACEUTICAL INGREDIENTS

(71) Applicant: Corning Incorporated, Corning, NY (US)

(72) Inventors: Wendell Porter Weeks, Corning, NY (US); Robert Anthony Schaut, Painted Post, NY (US); Steven Edward DeMartino, Painted Post, NY (US); John Stephen Peanasky, Big Flats, NY (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/660,690

(22) Filed: Oct. 25, 2012

(65) Prior Publication Data

US 2013/0196094 A1    Aug. 1, 2013

Related U.S. Application Data

(60) Provisional application No. 61/551,163, filed on Oct. 25, 2011, provisional application No. 61/656,998, filed on Jun. 7, 2012.

(51) Int. Cl.
*C03C 4/00* (2006.01)
*A61J 1/00* (2006.01)
(Continued)

(52) U.S. Cl.
CPC ............... *A61J 1/00* (2013.01); *A61K 39/3955* (2013.01); *C03C 3/087* (2013.01); *C03C 3/091* (2013.01); *C03C 4/20* (2013.01); *C03C 21/002* (2013.01); *Y10T 428/131* (2015.01)

(58) Field of Classification Search
CPC .......... A61J 1/00; C03C 3/076; C03C 3/087; C03C 3/083; C03C 4/20; C03C 21/00; C03C 21/001; C03C 21/002; B65D 1/02; B65D 1/0207
USPC ........... 428/34.4; 501/62, 69, 70, 72; 206/828
See application file for complete search history.

(56) References Cited

U.S. PATENT DOCUMENTS 3,490,885 A    1/1970    Hammer
3,772,135 A    11/1973   Hara et al.
(Continued)

FOREIGN PATENT DOCUMENTS

CN    101717189 A    6/2010
DE    29702816 U1    4/1997
(Continued)

OTHER PUBLICATIONS

Drugs.com, "Neulasta®," Sep. 13, 2010.*
(Continued)

*Primary Examiner* — Ellen S Wood
(74) *Attorney, Agent, or Firm* — Michael G. Panian

(57) ABSTRACT

The present invention is based, at least in part, on the identification of a pharmaceutical container formed, at least in part, of a glass composition which exhibits a reduced propensity to delaminate, i.e., a reduced propensity to shed glass particulates. As a result, the presently claimed containers are particularly suited for storage of pharmaceutical compositions and, specifically, a pharmaceutical solution comprising a pharmaceutically active ingredient, for example, NEUPOGEN® (filgrastim), NEULASTA® (pegfilgrastim), (epoetin alfa) or ENBREL® (etanercept).

43 Claims, 4 Drawing Sheets

(51) Int. Cl.
- *A61K 39/395* (2006.01)
- *C03C 3/087* (2006.01)
- *C03C 3/091* (2006.01)
- *C03C 21/00* (2006.01)
- *C03C 4/20* (2006.01)

(56) References Cited

U.S. PATENT DOCUMENTS

| | | | |
|---|---|---|---|
| 3,844,754 A | 10/1974 | Grubb et al. | |
| 4,065,317 A * | 12/1977 | Baak et al. | 501/70 |
| 4,689,085 A | 8/1987 | Plueddemann | |
| 5,114,757 A | 5/1992 | Linde et al. | |
| 5,286,527 A | 2/1994 | Blum et al. | |
| 5,547,929 A | 8/1996 | Anderson, Jr. et al. | |
| 5,547,933 A | 8/1996 | Lin | |
| 5,580,755 A | 12/1996 | Souza | |
| 5,582,823 A | 12/1996 | Souza | |
| 5,605,690 A | 2/1997 | Jacobs et al. | |
| 5,656,722 A | 8/1997 | Dorschug | |
| 5,721,181 A | 2/1998 | Sehgal et al. | |
| 5,736,476 A | 4/1998 | Watzke et al. | |
| 5,756,349 A | 5/1998 | Lin | |
| 5,824,784 A | 10/1998 | Kinstler et al. | |
| 5,854,153 A | 12/1998 | Kohli | |
| 5,955,422 A | 9/1999 | Lin | |
| RE36,755 E | 6/2000 | Smith et al. | |
| 6,096,432 A | 8/2000 | Sakaguchi et al. | |
| 6,214,429 B1 | 4/2001 | Zou et al. | |
| 6,472,068 B1 | 10/2002 | Glass et al. | |
| 6,518,211 B1 | 2/2003 | Bradshaw et al. | |
| 6,561,275 B2 | 5/2003 | Glass et al. | |
| 6,630,420 B1 | 10/2003 | Naumann et al. | |
| 6,794,323 B2 | 9/2004 | Peuchert et al. | |
| 6,818,576 B2 | 11/2004 | Ikenishi et al. | |
| RE38,743 E | 6/2005 | Debrie | |
| 6,939,819 B2 | 9/2005 | Usui et al. | |
| 7,087,307 B2 | 8/2006 | Nagashima et al. | |
| 7,315,125 B2 | 1/2008 | Kass | |
| 7,470,999 B2 | 12/2008 | Saito et al. | |
| 7,476,652 B2 | 1/2009 | Brunner-Schwarz et al. | |
| 7,915,225 B2 | 3/2011 | Finck | |
| 8,551,898 B2 | 10/2013 | Danielson et al. | |
| 8,753,994 B2 | 6/2014 | Danielson et al. | |
| 2004/0096588 A1 | 5/2004 | Brandt | |
| 2006/0154891 A1 | 7/2006 | Schridde et al. | |
| 2007/0004580 A1 | 1/2007 | Kass | |
| 2007/0010700 A1 * | 1/2007 | Bensmann et al. | 588/1 |
| 2007/0065366 A1 * | 3/2007 | Soliani Raschini et al. | 424/44 |
| 2007/0123410 A1 | 5/2007 | Morena et al. | |
| 2007/0157919 A1 | 7/2007 | Marandon | |
| 2007/0191207 A1 | 8/2007 | Danielson et al. | |
| 2008/0281260 A1 | 11/2008 | William et al. | |
| 2008/0308444 A1 | 12/2008 | McClain et al. | |
| 2009/0163342 A1 | 6/2009 | Kolberg et al. | |
| 2009/0197088 A1 | 8/2009 | Murata | |
| 2009/0275462 A1 | 11/2009 | Murata | |
| 2009/0325776 A1 | 12/2009 | Murata | |
| 2010/0035745 A1 | 2/2010 | Murata | |
| 2010/0047521 A1 | 2/2010 | Amin et al. | |
| 2010/0120603 A1 | 5/2010 | Morena et al. | |
| 2010/0255061 A1 | 10/2010 | de Juan, Jr. et al. | |
| 2010/0317506 A1 | 12/2010 | Fechner et al. | |
| 2011/0014475 A1 | 1/2011 | Murata | |
| 2011/0017297 A1 | 1/2011 | Aitken et al. | |
| 2011/0045960 A1 | 2/2011 | Fechner et al. | |
| 2011/0045961 A1 | 2/2011 | Dejneka et al. | |
| 2011/0062619 A1 | 3/2011 | Laine et al. | |
| 2011/0071012 A1 | 3/2011 | Kondo et al. | |
| 2011/0091704 A1 | 4/2011 | Akiba et al. | |
| 2011/0098172 A1 | 4/2011 | Brix | |
| 2011/0123832 A1 | 5/2011 | Matsumoto et al. | |
| 2011/0159318 A1 | 6/2011 | Endo et al. | |
| 2011/0177987 A1 | 7/2011 | Lenting et al. | |
| 2011/0274916 A1 | 11/2011 | Murata | |
| 2012/0199203 A1 | 8/2012 | Nishizawa et al. | |
| 2012/0208309 A1 | 8/2012 | Tsujimura et al. | |
| 2012/0297829 A1 | 11/2012 | Endo et al. | |
| 2013/0004758 A1 | 1/2013 | Dejneka et al. | |
| 2013/0011650 A1 | 1/2013 | Akiba et al. | |
| 2013/0101596 A1 | 4/2013 | DeMartino et al. | |
| 2013/0101764 A1 | 4/2013 | Schaut et al. | |
| 2013/0101766 A1 | 4/2013 | Danielson et al. | |
| 2013/0101853 A1 | 4/2013 | Drake et al. | |
| 2013/0196094 A1 | 8/2013 | Weeks et al. | |
| 2013/0196095 A1 | 8/2013 | Weeks et al. | |
| 2013/0196096 A1 | 8/2013 | Weeks et al. | |
| 2013/0196097 A1 | 8/2013 | Weeks et al. | |
| 2013/0202823 A1 | 8/2013 | Weeks et al. | |
| 2013/0213848 A1 | 8/2013 | Weeks et al. | |
| 2013/0216742 A1 | 8/2013 | DeMartino et al. | |
| 2014/0023865 A1 | 1/2014 | Comte et al. | |

FOREIGN PATENT DOCUMENTS

| | | |
|---|---|---|
| DE | 102004011009 A1 | 9/2005 |
| EP | 0515801 A1 | 12/1992 |
| EP | 1074521 A2 | 2/2001 |
| EP | 2031124 A1 | 3/2009 |
| EP | 2540682 A1 | 1/2013 |
| GB | 966731 A | 8/1964 |
| GB | 2335423 A | 9/1999 |
| IN | 231117 | 3/2009 |
| JP | 7223845 | 8/1995 |
| JP | 11314931 | 11/1999 |
| JP | 2000007372 A | 1/2000 |
| JP | 2001180969 A | 7/2001 |
| JP | 2001192239 A | 7/2001 |
| JP | 2001229526 A | 8/2001 |
| JP | 2001236634 A | 8/2001 |
| JP | 2002003241 A | 1/2002 |
| JP | 2002025762 A | 1/2002 |
| JP | 2002249340 A | 9/2002 |
| JP | 2004131314 A | 4/2004 |
| JP | 2008195602 A | 8/2008 |
| JP | 2010059038 A | 3/2010 |
| KR | 630309 | 5/2006 |
| RO | 83460 A2 | 3/1984 |
| SU | 990700 A1 | 1/1983 |
| WO | WO-2007025932 A2 | 3/2007 |
| WO | WO-2008050500 A1 | 5/2008 |
| WO | WO-2008143999 A1 | 11/2008 |
| WO | WO-2009002660 A2 | 12/2008 |
| WO | WO-2010084670 A1 | 7/2010 |
| WO | WO-2011049146 A1 | 4/2011 |
| WO | WO-2011069338 A1 | 6/2011 |
| WO | WO-2011103798 A1 | 9/2011 |
| WO | WO-2011103799 A1 | 9/2011 |
| WO | WO-2011145661 A1 | 11/2011 |
| WO | WO-2012026290 A1 | 3/2012 |
| WO | WO-2012124757 A1 | 9/2012 |
| WO | WO-2013063290 A1 | 5/2013 |

OTHER PUBLICATIONS

Drugs.com, "Enbrel," May 28, 2010.*
Roche Consumer Medicine Information, "Neupogen®," Feb. 3, 2010.*
Pharmaceutical Drug Manufacturers, "Erythropoietin Injection," Sep. 18, 2008.*
Adams RA. Formal discussion: the role of transplantation in the experimental investigation of human leukemia and lymphoma. Cancer Res. Dec. 1967;27(12):2479-82.
Barrowcliffe TW, et al., Anticoagulant activities of lung and mucous heparins. Thromb Res. Jan. 1978;12(1):27-36.
Beum PV et al., Three new assays for rituximab based on its immunological activity or antigenic properties: analyses of sera and plasmas of RTX-treated patients with chronic lymphocytic leukemia and other B cell lymphomas. J Immunol Methods. Jun. 2004;289(1-2):97-109.
Brunner KT et al. Quantitative assay of the lytic action of immune lymphoid cells on 51-Cr-labelled allogeneic target cells in vitro; inhibition by isoantibody and by drugs. Immunology. Feb. 1968;14(2):181-96.

(56) References Cited

OTHER PUBLICATIONS

Casset et al., "A peptide mimetic of an anti-CD4 monoclonal antibody by rational design", Biochem Biophys Res Commun. Jul. 18, 2003; vol. 307, No. 1, pp. 198-205.
Corrected Notice of Allowance mailed Sep. 11, 2013, relating to U.S. Appl. No. 13/660,394, filed Oct. 25, 2012.
Cortez-Retamozo et al., "Efficient cancer therapy with a nanobody-based conjugate", Cancer Research, Apr. 15, 2004, vol. 64, No. 8, pp. 2853-2857.
Cotes PM, et al., Bio-assay of erythropoietin in mice made polycythaemic by exposure to air at a reduced pressure. Nature. Sep. 9, 1961;191:1065-7.
Database WPI Week 198434 Thomsen Scientific, London, GB; AN 1984-211366 XP002690017.
Davis-Smyth T et al., the second immunoglobulin-like domain of the VEGF tyrosine kinase receptor Flt-1 determines ligand binding and may initiate a signal transduction cascade. EMBO J. Sep. 16, 1996;15(18):4919-27.
Drugs.com, Enbrel, May 28, 2010.
Drugs.com, Neulasta®, Sep. 13, 2010.
Fassina, G., "Complementary peptides as antibody mimetics for protein purification and assay", Immunomethods, Oct. 1994; vol. 5, No. 2, pp. 121-129.
Ferrara N, et al., Vascular endothelial growth factor is essential for corpus luteum angiogenesis. Nat Med. Mar. 1998;4(3):336-40.
Goldwasser E, et al., An assay for erythropoietin in vitro at the milliunit level. Endocrinology. Aug. 1975;97(2):315-23.
Hammond D, et al., Production, utilization and excretion of erythropoietin. I. Chronic anemias. II. Aplastic crisis. 3. Erythropoietic effects of normal plasma. Ann N Y Acad Sci. Mar. 29, 1968;149(1):516-27.
Holash J, et al., VEGF-Trap: a VEGF blocker with potent antitumor effects. Proc Natl Acad Sci U S A. Aug. 20, 2002;99(17):11393-8.
Horton RM et al., Engineering hybrid genes without the use of restriction enzymes: gene splicing by overlap extension. Gene. Apr. 15, 1989;77(1):61-8.
Humana Abbreviated Formulary List of Covered Drugs, 2010 Prescription Drug Guide.
International Search Report & Written Opinion relating to PCT/US2012/061940 filed Oct. 25, 2012; Mail Date: Jan. 30, 2013.
International Search Report & Written Opinion relating to PCT/US2012/061943 filed Oct. 25, 2012; Mail Date: Jan. 30, 2013.
International Search Report & Written Opinion relating to PCT/US2012/061946 filed Oct. 25, 2012; Mail Date: Jan. 30, 2013.
International Search Report & Written Opinion relating to PCT/US2012/061949 filed Oct. 25, 2012; Mail Date: Jan. 30, 2013.
International Search Report & Written Opinion relating to PCT/US2012/061953 filed Oct. 25, 2012; Mail Date: Jan. 30, 2013.
International Search Report & Written Opinion relating to PCT/US2012/061956 filed Oct 25, 2012; Mail Date: Jan. 30, 2013.
International Search Report & Written Opinion relating to PCT/US2012/061958 filed Oct. 25, 2012; Mail Date: Jan. 30, 2013.
International Search Report & Written Opinion relating to PCT/US2013/048589 filed Jun. 28, 2013; Mail Date: Oct. 28, 2013.
International Search Report relating to PCT/US2012/061867; Mail Date: Jan. 30, 2013.
International Search Report relating to PCT/US2012/061939; Mail Date: Jan. 30, 2013.
IPRP & Written Opinion relating to PCT/US2012/061940 filed Oct. 25, 2012; Mail Date: May 8, 2014.
IPRP & Written Opinion relating to PCT/US2012/061943 filed Oct. 25, 2012; Mail Date: May 8, 2014.
IPRP & Written Opinion relating to PCT/US2012/061946 filed Oct. 25, 2012; Mail Date: May 8, 2014.
IPRP & Written Opinion relating to PCT/US2012/061949 filed Oct. 25, 2012; Mail Date: May 8, 2014.
IPRP & Written Opinion relating to PCT/US2012/061953 filed Oct. 25, 2012; Mail Date: May 8, 2014.
IPRP & Written Opinion relating to PCT/US2012/061956, filed Oct. 25, 2012; Mail date: May 8, 2014.
IPRP & Written Opinion relating to PCT/US2012/061958 filed Oct. 25, 2012; Mail Date: May 8, 2014.
Karch, AM, "2006 Lippincott's Nursing Drug Guide," Publisher: Lippincott Williams & Wilkins, ISBN: 1582554382, 2006.
Lane DA, et al., Anticoagulant activities of four unfractionated and fractionated heparins. Thromb Res. Feb. 1978;12(2):257-71.
Lichtlen P, Lam TT, Nork TM, Streit T, Urech DM. Relative contribution of VEGF and TNF-alpha in the cynomolgus laser-induced CNV model: comparing the efficacy of bevacizumab, adalimumab, and SBA105. Invest Ophthalmol Vis Sci. Sep. 2010;51(9):4738-45.
Machine translation CN101717189 Abstract.
Machine translation DE102004011009.
Machine translation JP2002025762 Abstract.
Machine translation JP2004131314.
Metcalf D. Clonal extinction of myelomonocytic leukemic cells by serum from mice injected with endotoxin. Int J Cancer. Feb. 15, 1980;25(2):225-33.
Murphy, D. B. and Davidson, M. W., "Differential Interference Contrast (DIC) Microscopy and Modulation Contrast" form Fundamentals of Light Microscopy and Electronic Imaging Published 2001, Publisher, Wiley, pp. 153-168.
Non-Final Office Action mailed Mar. 14, 2013, relating to U.S. Appl. No. 13/660,394, filed Oct. 25, 2012.
Notice of Allowance mailed Jun. 27, 2013, relating to U.S. Appl. No. 13/660,394, filed Oct. 25, 2012.
Pharmaceutical Drug Manufacturers, Erythropoietin Injection, Sep. 18, 2008.
Randle PJ., "Assay of plasma insulin activity by the rat-diaphragm method", British Medical Journal, May 29, 1954, vol. 1 (4873), pp. 1237-1240.
Reynolds et al., "Glass Delamination and Breakage", Bioprocess International, Dec. 1, 2011, vol. 9, No. 11, pp. 52-57.
Ribel U, Subcutaneous absorption of insulin analogues. In Frontiers in Insulin Pharmacology, Berger M, Gries FA (eds), Thieme Verlag, pp. 70-77 (1993).
Ribel U., et al., The pig as a model for subcutaneous insulin absorption in man. Serrano_Rios, M and Lefebvre, P.J. 891-896. 1985. Amsterdam; New York; Oxford, Elsevier Science Publishers. 1985 (Conference Proceeding).
Roche Consumer Medicine Information, Neupogen®, Feb. 3, 2010.
Saragovi et al., "Design and synthesis of a mimetic from an antibody complementarity-determining region", Science, Aug. 16, 1991, vol. 253, No. 5021, pp. 792-795.
Silva M, et al., Erythropoietin can induce the expression of bcl-x(L) through Stat5 in erythropoietin-dependent progenitor cell lines. J Biol Chem. Aug. 6, 1999;274(32):22165-9.
Teien AN, et al., Evaluation of an amidolytic heparin assay method: increased sensitivity by adding purified antithrombin III. Thromb Res. Mar. 1977;10(3):399-410.
Ternant D, et al., An enzyme-linked immunosorbent assay for therapeutic drug monitoring of infliximab. Ther Drug Monit. Apr. 2006;28(2):169-74.
U.S. Food and Drug Administration, Package Insert HUMIRA (adalimumab) Abbott Laboratories, 2010.
Ueda et al., "Age-dependent changes in phenotypes and candidate gene analysis in a polygenic animal model of Type II diabetes mellitus; NSY mouse" Diabetologia, Jul. 2000, vol. 43, Issue 7, pp. 932-938.
Wen, Zai-Qing et al., "Nondestructive detection of glass vial inner surface morphology with differential interference contrast microscopy", Journal of Pharmaceutical Sciences, Apr. 2012, vol. 101, Issue 4, pp. 1378-1384.
Yu L et al., Interaction between bevacizumab and murine VEGF-A: a reassessment. Invest Ophthalmol Vis Sci. Feb. 2008;49(2):522-7.

\* cited by examiner

DELAMINATION RESISTANT PHARMACEUTICAL GLASS CONTAINERS CONTAINING ACTIVE PHARMACEUTICAL INGREDIENTS

CROSS REFERENCE TO RELATED APPLICATIONS

The present application claims priority to U.S. Provisional Patent Application Ser. No. 61/551,163, filed Oct. 25, 2011, entitled "Glass Compositions With Improved Chemical and Mechanical Durability," and U.S. Provisional Patent Application No. 61/656,998, filed Jun. 7, 2012, entitled "De-lamination Resistant Glass Containers"; the entirety of each of which are hereby incorporated by reference herein.

FIELD OF THE INVENTION

The present specification generally relates to pharmaceutical containers and, more specifically, to chemically and mechanically durable pharmaceutical containers that are delamination resistant and formed, at least in part, of a glass composition.

BACKGROUND

The design of a packaged pharmaceutical composition generally seeks to provide an active pharmaceutical ingredient (API) in a suitable package that is convenient to use, that maintains the stability of the API over prolonged storage, and that ultimately allows for the delivery of efficacious, stable, active, nontoxic and nondegraded API.

Most packaged formulations are complex physico-chemical systems, through which the API is subject to deterioration by a variety of chemical, physical, and microbial reactions. Interactions between drugs, adjuvants, containers, and/or closures may occur, which can lead to the inactivation, decomposition and/or degradation of the API.

Historically, glass has been used as the preferred material for packaging pharmaceuticals because of its hermeticity, optical clarity and excellent chemical durability relative to other materials. Specifically, the glass used in pharmaceutical packaging must have adequate chemical durability so as not to affect the stability of the pharmaceutical compositions contained therein. Glasses having suitable chemical durability include those glass compositions within the ASTM standard 'Type 1B' glass compositions which have a proven history of chemical durability.

However, use of glass for such applications is limited by the mechanical performance of the glass. Specifically, in the pharmaceutical industry, glass breakage is a safety concern for the end user as the broken package and/or the contents of the package may injure the end user. Further, non-catastrophic breakage (i.e., when the glass cracks but does not break) may cause the contents to lose their sterility which, in turn, may result in costly product recalls.

One approach to improving the mechanical durability of the glass package is to thermally temper the glass package. Thermal tempering strengthens glass by inducing a surface compressive stress during rapid cooling after forming. This technique works well for glass articles with flat geometries (such as windows), glass articles with thicknesses>2 mm, and glass compositions with high thermal expansion. However, pharmaceutical glass packages typically have complex geometries (vial, tubular, ampoule, etc.), thin walls (~1-1.5 mm), and are produced from low expansion glasses (30-55× $10^{-7}K^{-1}$) making glass pharmaceutical packages unsuitable for strengthening by thermal tempering.

Chemical tempering also strengthens glass by the introduction of surface compressive stress. The stress is introduced by submerging the article in a molten salt bath. As ions from the glass are replaced by larger ions from the molten salt, a compressive stress is induced in the surface of the glass. The advantage of chemical tempering is that it can be used on complex geometries, thin samples, and is relatively insensitive to the thermal expansion characteristics of the glass substrate. However, glass compositions which exhibit a moderate susceptibility to chemical tempering generally exhibit poor chemical durability and vice-versa.

Finally, glass compositions commonly used in pharmaceutical packages, e.g., Type 1a and Type 1b glass, further suffer from a tendency for the interior surfaces of the pharmaceutical package to shed glass particulates or "delaminate" following exposure to pharmaceutical solutions. Such delamination often destabilizes the active pharmaceutical ingredient (API) present in the solution, thereby rendering the API therapeutically ineffective or unsuitable for therapeutic use.

Delamination has caused the recall of multiple drug products over the last few years (see, for example, Reynolds et al., (2011) BioProcess International 9(11) pp. 52-57). In response to the growing delamination problem, the U.S. Food and Drug Administration (FDA) has issued an advisory indicating that the presence of glass particulate in injectable drugs can pose a risk.

The advisory states that, "[t]here is potential for drugs administered intravenously that contain these fragments to cause embolic, thrombotic and other vascular events; and subcutaneously to the development of foreign body granuloma, local injections site reactions and increased immunogenicity."

Accordingly, a recognized need exists for alternative glass containers for packaging of pharmaceutical compositions which exhibit a reduced propensity to delaminate.

SUMMARY

In one aspect, the present invention is directed to a delamination resistant pharmaceutical container formed, at least in part, of a glass composition including from about 70 mol. % to about 80 mol. % $SiO_2$; from about 3 mol. % to about 13 mol. % alkaline earth oxide; X mol. % $Al_2O_3$; and Y mol. % alkali oxide, wherein the alkali oxide includes $Na_2O$ in an amount greater than about 8 mol. %, wherein the ratio of Y:X is greater than 1, and the glass composition is free of boron and compounds of boron.

In one embodiment, the $SiO_2$ is present in an amount less than or equal to 78 mol. %.

In one embodiment, the amount of the alkaline earth oxide is greater than or equal to about 4 mol. % and less than or equal to about 8 mol. %. In a particular embodiment, the alkaline earth oxide includes MgO and CaO and has a ratio (CaO (mol. %)/(CaO (mol. %)+MgO (mol. %))) that is less than or equal to 0.5. In a particular embodiment, the alkaline earth oxide includes from about 0.1 mol. % to less than or equal to about 1.0 mol. % CaO. In a particular embodiment, the alkaline earth oxide includes from about 3 mol. % to about 7 mol. % MgO.

In another embodiment, the alkali oxide includes greater than or equal to about 9 mol. % $Na_2O$ and less than or equal to about 15 mol. % $Na_2O$. In another embodiment, the alkali oxide further includes $K_2O$ in an amount less than or equal to about 3 mol. %. In a particular embodiment, the alkali oxide includes $K_2O$ in an amount greater than or equal to about 0.01 mol. % and less than or equal to about 1.0 mol. %.

In one embodiment, X is greater than or equal to about 2 mol. % and less than or equal to about 10 mol. %. In a particular embodiment, the ratio of Y:X is less than or equal to 2. In a particular embodiment, the ratio of Y:X is greater than or equal to 1.3 and less than or equal to 2.0.

In another embodiment, the glass composition is free of phosphorous and compounds of phosphorous.

In one embodiment, the glass composition has a type HGB1 hydrolytic resistance according to ISO 719. Alternatively or in addition, the glass composition has a type HGA1 hydrolytic resistance according to ISO 720 after ion exchange strengthening. Alternatively or in addition, the glass composition has a type HGA1 hydrolytic resistance according to ISO 720 before and after ion exchange strengthening. Alternatively or in addition, the glass composition has at least a class S3 acid resistance according to DIN 12116. Alternatively or in addition, the glass composition has at least a class A2 base resistance according to ISO 695.

In one embodiment, the glass composition is ion exchange strengthened.

In another embodiment, the composition further includes a compressive stress layer with a depth of layer greater than or equal to 10 µm and a surface compressive stress greater than or equal to 250 MPa.

In another aspect, the present invention provides a delamination resistant pharmaceutical container formed, at least in part, of a glass composition including from about 72 mol. % to about 78 mol. % $SiO_2$; from about 4 mol. % to about 8 mol. % alkaline earth oxide; X mol. % $Al_2O_3$, wherein X is greater than or equal to about 4 mol. % and less than or equal to about 8 mol. %; and Y mol. % alkali oxide, wherein the alkali oxide includes $Na_2O$ in an amount greater than or equal to about 9 mol. % and less than or equal to about 15 mol. %, wherein the ratio of Y:X is greater than 1, and the glass composition is free of boron and compounds of boron.

In a particular embodiment, the ratio of Y:X is less than or equal to about 2. In a particular embodiment, the ratio of Y:X is greater than or equal to about 1.3 and less than or equal to about 2.0.

In one embodiment, the alkaline earth oxide includes MgO and CaO and has a ratio (CaO (mol. %)/(CaO (mol. %)+MgO (mol. %))) less than or equal to 0.5.

In another embodiment, the alkali oxide includes $K_2O$ in an amount greater than or equal to about 0.01 mol. % and less than or equal to about 1.0 mol. %.

In another aspect, the present invention provides a delamination resistant pharmaceutical container formed, at least in part, of a glass composition including from about 68 mol. % to about 80 mol. % $SiO_2$; from about 3 mol. % to about 13 mol. % alkaline earth oxide; X mol. % $Al_2O_3$; Y mol. % alkali oxide, wherein the alkali oxide includes $Na_2O$ in an amount greater than about 8 mol. %; and $B_2O_3$, wherein the ratio ($B_2O_3$ (mol. %)/(Y mol. %–X mol. %) is greater than 0 and less than 0.3, and the ratio of Y:X is greater than 1.

In one embodiment, the amount of $SiO_2$ is greater than or equal to about 70 mol. %.

In one embodiment, the amount of alkaline earth oxide is greater than or equal to about 4 mol. % and less than or equal to about 8 mol. %. In a particular embodiment, the alkaline earth oxide includes MgO and CaO and has a ratio (CaO (mol. %)/(CaO (mol. %)+MgO (mol. %))) less than or equal to 0.5. In a particular embodiment, the alkaline earth oxide includes CaO in an amount greater than or equal to about 0.1 mol. % and less than or equal to about 1.0 mol. %. In a particular embodiment, the alkaline earth oxide includes from about 3 mol. % to about 7 mol. % MgO.

In one embodiment, the alkali oxide is greater than or equal to about 9 mol. % $Na_2O$ and less than or equal to about 15 mol. % $Na_2O$. In a particular embodiment, the alkali oxide further includes $K_2O$ in a concentration less than or equal to about 3 mol. %. In another embodiment, the alkali oxide further includes $K_2O$ in a concentration greater than or equal to about 0.01 mol. % and less than or equal to about 1.0 mol. %.

In another embodiment, the pharmaceutical container has a ratio ($B_2O_3$ (mol. %)/(Y mol. %–X mol. %) less than 0.2. In a particular embodiment, the amount of $B_2O_3$ is less than or equal to about 4.0 mol. %. In another embodiment, the amount of $B_2O_3$ is greater than or equal to about 0.01 mol. %.

In one embodiment, X is greater than or equal to about 2 mol. % and less than or equal to about 10 mol. %. In a particular embodiment, the ratio of Y:X is less than or equal to 2. In another embodiment, the ratio of Y:X is greater than 1.3.

In one embodiment, the glass composition is free of phosphorous and compounds of phosphorous.

In one embodiment, the glass composition has a type HGB1 hydrolytic resistance according to ISO 719. Alternatively or in addition, the glass composition has a type HGA1 hydrolytic resistance according to ISO 720 after ion exchange strengthening. Alternatively or in addition, the glass composition has a type HGA1 hydrolytic resistance according to ISO 720 before and after ion exchange strengthening. Alternatively or in addition, the glass composition has at least a class S3 acid resistance according to DIN 12116. Alternatively or in addition, the glass composition has at least a class A2 base resistance according to ISO 695.

In one embodiment, the glass composition is ion exchange strengthened.

In another embodiment, the composition further includes a compressive stress layer with a depth of layer greater than or equal to 10 µm and a surface compressive stress greater than or equal to 250 MPa.

In one embodiment of any of the foregoing aspects of the invention, the pharmaceutical container further includes a pharmaceutical composition having an active pharmaceutical ingredient. In a particular embodiment, the pharmaceutical composition includes a citrate or phosphate buffer, for example, sodium citrate, SSC, monosodium phosphate or disodium phosphate. Alternatively or in addition, the pharmaceutical composition has a pH between about 7 and about 11, between about 7 and about 10, between about 7 and about 9, or between about 7 and about 8.

In one embodiment of any of the foregoing aspects of the invention, the active pharmaceutical ingredient is recombinant human granulocyte-colony stimulating factor, or an analog thereof. In one embodiment, the pharmaceutical composition is NEUPOGEN® (Filgrastim).

In one embodiment of any of the foregoing aspects of the invention, the active pharmaceutical ingredient is PEGylated recombinant human granulocyte-colony stimulating factor, or an analog thereof. In a particular embodiment, the pharmaceutical composition is NEULASTA® (Pegfilgrastim).

In one embodiment of any of the foregoing aspects of the invention, the active pharmaceutical ingredient is an erythropoiesis-stimulating glycoprotein. In a particular embodiment, the pharmaceutical composition is EPOGEN® (epoetin alfa).

In one embodiment of any of the foregoing aspects of the invention, the active pharmaceutical ingredient is a fusion protein of TNF Receptor 2 and IgG1. In a particular embodiment, the pharmaceutical composition is ENBREL (etanercept).

In a particular aspect, the present invention provides a delamination resistant pharmaceutical container formed, at least in part, of a glass composition including about 76.8 mol. % $SiO_2$; about 6.0 mol. % $Al_2O_3$; about 11.6 mol. % $Na_2O$; about 0.1 mol. % $K_2O$; about 4.8 mol. % MgO; and about 0.5 mol. % CaO, wherein the glass composition is free of boron and compounds of boron; and wherein the pharmaceutical container further comprises a pharmaceutical composition selected from the group consisting of NEUPOGEN® (filgrastim), NEULASTA® (pegfilgrastim), EPOGEN® (epoetin alfa) and ENBREL® (etanercept).

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
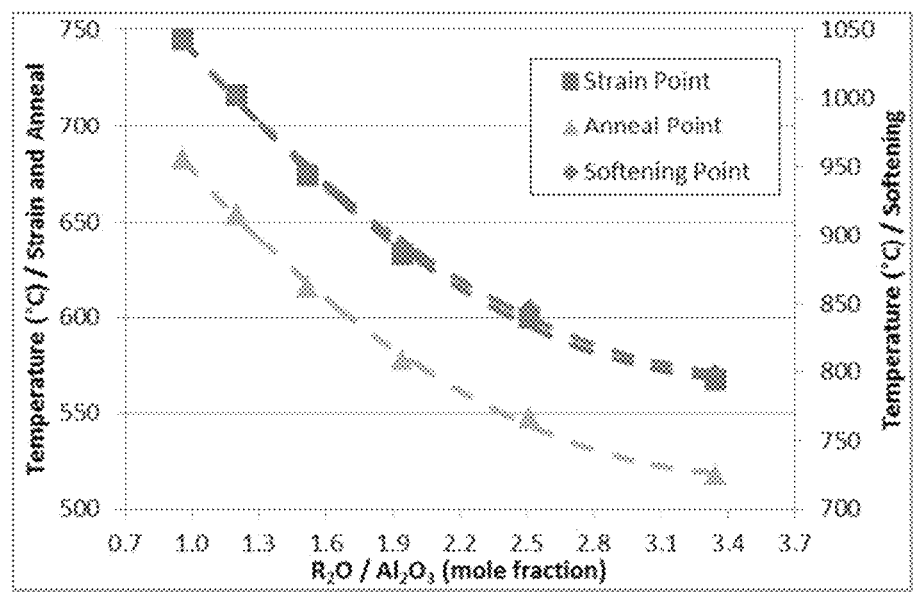
FIG. 1 graphically depicts the relationship between the ratio of alkali oxides to alumina (x-axis) and the strain point, annealing point, and softening point (y-axes) of inventive and comparative glass compositions.

The present invention is based, at least in part, on the identification of a pharmaceutical container formed, at least in part, of a glass composition which exhibits a reduced propensity to delaminate, i.e., a reduced propensity to shed glass particulates. As a result, the presently claimed containers are particularly suited for storage, maintenance and/or delivery of therapeutically efficacious pharmaceutical compositions and, in particular pharmaceutical solutions comprising active pharmaceutical ingredients, for example, NEUPOGEN® (filgrastim), NEULASTA® (pegfilgrastim), EPOGEN® (epoetin alfa) or ENBREL® (etanercept).

Conventional glass containers or glass packages for containing pharmaceutical compositions are generally formed from glass compositions which are known to exhibit chemical durability and low thermal expansion, such as alkali borosilicate glasses. While alkali borosilicate glasses exhibit good chemical durability, container manufacturers have sporadically observed silica-rich glass flakes dispersed in the solution contained in the glass containers as a result of delamination, particularly when the solution has been stored in direct contact with the glass surface for long time periods (months to years).

Delamination refers to a phenomenon in which glass particles are released from the surface of the glass following a series of leaching, corrosion, and/or weathering reactions. In general, the glass particles are silica-rich flakes of glass which originate from the interior surface of the package as a result of the leaching of modifier ions into a solution contained within the package. These flakes may generally be from about 1 nm to 2 μm thick with a width greater than about 50 μm.

It has heretofore been hypothesized that delamination is due to the phase separation which occurs in alkali borosilicate glasses when the glass is exposed to the elevated temperatures used for reforming the glass into a container shape.

However, it is now believed that the delamination of the silica-rich glass flakes from the interior surfaces of the glass containers is due to the compositional characteristics of the glass container in its as-formed condition. Specifically, the high silica content of alkali borosilicate glasses increases the melting temperature of the glass. However, the alkali and borate components in the glass composition melt and/or vaporize at much lower temperatures. In particular, the borate species in the glass are highly volatile and evaporate from the surface of the glass at the high temperatures necessary to melt and form the glass.

Specifically, glass stock is reformed into glass containers at high temperatures and in direct flames. The high temperatures cause the volatile borate species to evaporate from portions of the surface of the glass. When this evaporation occurs within the interior volume of the glass container, the volatilized borate species are re-deposited in other areas of the glass causing compositional heterogeneities in the glass container, particularly with respect to the bulk of the glass container. For example, as one end of a glass tube is closed to form the bottom or floor of the container, borate species may evaporate from the bottom portion of the tube and be re-deposited elsewhere in the tube. As a result, the areas of the container exposed to higher temperatures have silica-rich surfaces. Other areas of the container which are amenable to boron deposition may have a silica-rich surface with a boron-rich layer below the surface. Areas amenable to boron deposition are at a temperature greater than the anneal point of the glass composition but less than the hottest temperature the glass is subjected to during reformation when the boron is incorporated into the surface of the glass. Solutions contained in the container may leach the boron from the boron-rich layer. As the boron-rich layer is leached from the glass, the silica-rich surface begins to spall, shedding silica-rich flakes into the solution.

DEFINITIONS

The term "softening point," as used herein, refers to the temperature at which the viscosity of the glass composition is $1\times10^{7.6}$ poise.

The term "annealing point," as used herein, refers to the temperature at which the viscosity of the glass composition is $1\times10^{13}$ poise.

The terms "strain point" and "$T_{strain}$" as used herein, refers to the temperature at which the viscosity of the glass composition is $3\times10^{14}$ poise.

The term "CTE," as used herein, refers to the coefficient of thermal expansion of the glass composition over a temperature range from about room temperature (RT) to about 300° C.

In the embodiments of the glass compositions described herein, the concentrations of constituent components (e.g., $SiO_2$, $Al_2O_3$, and the like) are specified in mole percent (mol. %) on an oxide basis, unless otherwise specified.

The terms "free" and "substantially free," when used to describe the concentration and/or absence of a particular constituent component in a glass composition, means that the constituent component is not intentionally added to the glass composition. However, the glass composition may contain traces of the constituent component as a contaminant or tramp in amounts of less than 0.01 mol. %.

The term "chemical durability," as used herein, refers to the ability of the glass composition to resist degradation upon exposure to specified chemical conditions. Specifically, the chemical durability of the glass compositions described herein was assessed according to three established material testing standards: DIN 12116 dated March 2001 and entitled "Testing of glass—Resistance to attack by a boiling aqueous solution of hydrochloric acid—Method of test and classification"; ISO 695:1991 entitled "Glass—Resistance to attack by a boiling aqueous solution of mixed alkali—Method of test and classification"; and ISO 720:1985 entitled "Glass—Hydrolytic resistance of glass grains at 121 degrees C.—Method of test and classification." The chemical durability of the glass may also be assessed according to ISO 719:1985 "Glass—Hydrolytic resistance of glass grains at 98 degrees C.—Method of test and classification," in addition to the above referenced standards. The ISO 719 standard is a less rigorous version of the ISO 720 standard and, as such, it is believed that a glass which meets a specified classification of the ISO 720 standard will also meet the corresponding classification of the ISO 719 standard. The classifications associated with each standard are described in further detail herein.

Glass Compositions

Reference will now be made in detail to various embodiments of pharmaceutical containers formed, at least in part, of glass compositions which exhibit improved chemical and mechanical durability and, in particular, improved resistance to delamination. The glass compositions may also be chemically strengthened thereby imparting increased mechanical durability to the glass. The glass compositions described herein generally comprise silica ($SiO_2$), alumina ($Al_2O_3$), alkaline earth oxides (such as MgO and/or CaO), and alkali oxides (such as $Na_2O$ and/or $K_2O$) in amounts which impart chemical durability to the glass composition. Moreover, the alkali oxides present in the glass compositions facilitate chemically strengthening the glass compositions by ion exchange. Various embodiments of the glass compositions will be described herein and further illustrated with reference to specific examples.

The glass compositions described herein are alkali aluminosilicate glass compositions which generally include a combination of $SiO_2$, $Al_2O_3$, at least one alkaline earth oxide, and one or more alkali oxides, such as $Na_2O$ and/or $K_2O$. In some embodiments, the glass compositions may be free from boron and compounds containing boron. The combination of these components enables a glass composition which is resistant to chemical degradation and is also suitable for chemical strengthening by ion exchange. In some embodiments the glass compositions may further comprise minor amounts of one or more additional oxides such as, for example, $SnO_2$, $ZrO_2$, ZnO, $TiO_2$, $As_2O_3$ or the like. These components may be added as fining agents and/or to further enhance the chemical durability of the glass composition.

In the embodiments of the glass compositions described herein $SiO_2$ is the largest constituent of the composition and, as such, is the primary constituent of the resulting glass network. $SiO_2$ enhances the chemical durability of the glass and, in particular, the resistance of the glass composition to decomposition in acid and the resistance of the glass composition to decomposition in water. Accordingly, a high $SiO_2$ concentration is generally desired. However, if the content of $SiO_2$ is too high, the formability of the glass may be diminished as higher concentrations of $SiO_2$ increase the difficulty of melting the glass which, in turn, adversely impacts the formability of the glass. In the embodiments described herein, the glass composition generally comprises $SiO_2$ in an amount greater than or equal to 67 mol. % and less than or equal to about 80 mol. % or even less than or equal to 78 mol. %. In some embodiments, the amount of $SiO_2$ in the glass composition may be greater than about 68 mol. %, greater than about 69 mol. % or even greater than about 70 mol. %. In some other embodiments, the amount of $SiO_2$ in the glass composition may be greater than 72 mol. %, greater than 73 mol. % or even greater than 74 mol. %. For example, in some embodiments, the glass composition may include from about 68 mol. % to about 80 mol. % or even to about 78 mol. % $SiO_2$. In some other embodiments the glass composition may include from about 69 mol. % to about 80 mol. % or even to about 78 mol. % $SiO_2$. In some other embodiments the glass composition may include from about 70 mol. % to about 80 mol. % or even to about 78 mol. % $SiO_2$. In still other embodiments, the glass composition comprises $SiO_2$ in an amount greater than or equal to 70 mol. % and less than or equal to 78 mol. %. In some embodiments, $SiO_2$ may be present in the glass composition in an amount from about 72 mol. % to about 78 mol. %. In some other embodiments, $SiO_2$ may be present in the glass composition in an amount from about 73 mol. % to about 78 mol. %. In other embodiments, $SiO_2$ may be present in the glass composition in an amount from about 74 mol. % to about 78 mol. %. In still other embodiments, $SiO_2$ may be present in the glass composition in an amount from about 70 mol. % to about 76 mol. %.

The glass compositions described herein further include $Al_2O_3$. $Al_2O_3$, in conjunction with alkali oxides present in the glass compositions such as $Na_2O$ or the like, improves the susceptibility of the glass to ion exchange strengthening. In the embodiments described herein, $Al_2O_3$ is present in the glass compositions in X mol. % while the alkali oxides are present in the glass composition in Y mol. %. The ratio Y:X in the glass compositions described herein is greater than 1 in order to facilitate the aforementioned susceptibility to ion exchange strengthening. Specifically, the diffusion coefficient or diffusivity D of the glass composition relates to the rate at which alkali ions penetrate into the glass surface during ion exchange. Glasses which have a ratio Y:X greater than about 0.9 or even greater than about 1 have a greater diffusivity than glasses which have a ratio Y:X less than 0.9. Glasses in which the alkali ions have a greater diffusivity can obtain a greater depth of layer for a given ion exchange time and ion exchange temperature than glasses in which the alkali ions have a lower diffusivity. Moreover, as the ratio of Y:X increases, the strain point, anneal point, and softening point of the glass decrease, such that the glass is more readily formable. In addition, for a given ion exchange time and ion exchange temperature, it has been found that compressive stresses induced in glasses which have a ratio Y:X greater than about 0.9 and less than or equal to 2 are generally greater than those generated in glasses in which the ratio Y:X is less than 0.9 or greater than 2. Accordingly, in some embodiments, the ratio of Y:X is greater than 0.9 or even greater than 1. In some embodiments, the ratio of Y:X is greater than 0.9, or even greater than 1, and less than or equal to about 2. In still other embodiments, the ratio of Y:X may be greater than or equal to about 1.3 and less than or equal to about 2.0 in order to maximize the amount of compressive stress induced in the glass for a specified ion exchange time and a specified ion exchange temperature.

However, if the amount of $Al_2O_3$ in the glass composition is too high, the resistance of the glass composition to acid attack is diminished. Accordingly, the glass compositions described herein generally include $Al_2O_3$ in an amount greater than or equal to about 2 mol. % and less than or equal to about 10 mol. %. In some embodiments, the amount of $Al_2O_3$ in the glass composition is greater than or equal to about 4 mol. % and less than or equal to about 8 mol. %. In some other embodiments, the amount of $Al_2O_3$ in the glass composition is greater than or equal to about 5 mol. % to less than or equal to about 7 mol. %. In some other embodiments, the amount of $Al_2O_3$ in the glass composition is greater than or equal to about 6 mol. % to less than or equal to about 8 mol. %. In still other embodiments, the amount of $Al_2O_3$ in the glass composition is greater than or equal to about 5 mol. % to less than or equal to about 6 mol. %.

The glass compositions also include one or more alkali oxides such as $Na_2O$ and/or $K_2O$. The alkali oxides facilitate the ion exchangeability of the glass composition and, as such, facilitate chemically strengthening the glass. The alkali oxide may include one or more of $Na_2O$ and $K_2O$. The alkali oxides are generally present in the glass composition in a total concentration of Y mol. %. In some embodiments described herein, Y may be greater than about 2 mol. % and less than or equal to about 18 mol. %. In some other embodiments, Y may be greater than about 8 mol. %, greater than about 9 mol. %, greater than about 10 mol. % or even greater than about 11 mol. %. For example, in some embodiments described herein Y is greater than or equal to about 8 mol. % and less than or equal to about 18 mol. %. In still other embodiments, Y may be greater than or equal to about 9 mol. % and less than or equal to about 14 mol. %.

The ion exchangeability of the glass composition is primarily imparted to the glass composition by the amount of the alkali oxide $Na_2O$ initially present in the glass composition prior to ion exchange. Accordingly, in the embodiments of the glass compositions described herein, the alkali oxide present in the glass composition includes at least $Na_2O$. Specifically, in order to achieve the desired compressive strength and depth of layer in the glass composition upon ion exchange strengthening, the glass compositions include $Na_2O$ in an amount from about 2 mol. % to about 15 mol. % based on the molecular weight of the glass composition. In some embodiments the glass composition includes at least about 8 mol. % of $Na_2O$ based on the molecular weight of the glass composition. For example, the concentration of $Na_2O$ may be greater than 9 mol. %, greater than 10 mol. % or even greater than 11 mol. %. In some embodiments, the concentration of $Na_2O$ may be greater than or equal to 9 mol. % or even greater than or equal to 10 mol. %. For example, in some embodiments the glass composition may include $Na_2O$ in an amount greater than or equal to about 9 mol. % and less than or equal to about 15 mol. % or even greater than or equal to about 9 mol. % and less than or equal to 13 mol. %.

As noted above, the alkali oxide in the glass composition may further include $K_2O$. The amount of $K_2O$ present in the glass composition also relates to the ion exchangeability of the glass composition. Specifically, as the amount of $K_2O$ present in the glass composition increases, the compressive stress obtainable through ion exchange decreases as a result of the exchange of potassium and sodium ions. Accordingly, it is desirable to limit the amount of $K_2O$ present in the glass composition. In some embodiments, the amount of $K_2O$ is greater than or equal to 0 mol. % and less than or equal to 3 mol. %. In some embodiments, the amount of $K_2O$ is less or equal to 2 mol. % or even less than or equal to 1.0 mol. %. In embodiments where the glass composition includes $K_2O$, the $K_2O$ may be present in a concentration greater than or equal to about 0.01 mol. % and less than or equal to about 3.0 mol. % or even greater than or equal to about 0.01 mol. % and less than or equal to about 2.0 mol. %. In some embodiments, the amount of $K_2O$ present in the glass composition is greater than or equal to about 0.01 mol. % and less than or equal to about 1.0 mol. %. Accordingly, it should be understood that $K_2O$ need not be present in the glass composition. However, when $K_2O$ is included in the glass composition, the amount of $K_2O$ is generally less than about 3 mol. % based on the molecular weight of the glass composition.

The alkaline earth oxides present in the composition improve the meltability of the glass batch materials and increase the chemical durability of the glass composition. In the glass compositions described herein, the total mol. % of alkaline earth oxides present in the glass compositions is generally less than the total mol. % of alkali oxides present in the glass compositions in order to improve the ion exchangeability of the glass composition. In the embodiments described herein, the glass compositions generally include from about 3 mol. % to about 13 mol. % of alkaline earth oxide. In some of these embodiments, the amount of alkaline earth oxide in the glass composition may be from about 4 mol. % to about 8 mol. % or even from about 4 mol. % to about 7 mol. %.

The alkaline earth oxide in the glass composition may include MgO, CaO, SrO, BaO or combinations thereof. In some embodiments, the alkaline earth oxide includes MgO, CaO or combinations thereof. For example, in the embodiments described herein the alkaline earth oxide includes MgO. MgO is present in the glass composition in an amount which is greater than or equal to about 3 mol. % and less than or equal to about 8 mol. % MgO. In some embodiments, MgO may be present in the glass composition in an amount which is greater than or equal to about 3 mol. % and less than or equal to about 7 mol. % or even greater than or equal to 4 mol. % and less than or equal to about 7 mol. % by molecular weight of the glass composition.

In some embodiments, the alkaline earth oxide may further include CaO. In these embodiments CaO is present in the glass composition in an amount from about 0 mol. % to less than or equal to 6 mol. % by molecular weight of the glass composition. For example, the amount of CaO present in the glass composition may be less than or equal to 5 mol. %, less than or equal to 4 mol. %, less than or equal to 3 mol. %, or even less than or equal to 2 mol. %. In some of these embodiments, CaO may be present in the glass composition in an amount greater than or equal to about 0.1 mol. % and less than or equal to about 1.0 mol. %. For example, CaO may be present in the glass composition in an amount greater than or equal to about 0.2 mol. % and less than or equal to about 0.7 mol. % or even in an amount greater than or equal to about 0.3 mol. % and less than or equal to about 0.6 mol. %.

In the embodiments described herein, the glass compositions are generally rich in MgO, (i.e., the concentration of MgO in the glass composition is greater than the concentration of the other alkaline earth oxides in the glass composition including, without limitation, CaO). Forming the glass composition such that the glass composition is MgO-rich improves the hydrolytic resistance of the resultant glass, particularly following ion exchange strengthening. Moreover, glass compositions which are MgO-rich generally exhibit improved ion exchange performance relative to glass compositions which are rich in other alkaline earth oxides. Specifically, glasses formed from MgO-rich glass compositions generally have a greater diffusivity than glass compositions which are rich in other alkaline earth oxides, such as CaO. The greater diffusivity enables the formation of a deeper depth of layer in the glass. MgO-rich glass compositions also enable a higher compressive stress to be achieved in the surface of the glass compared to glass compositions which are rich in other alkaline earth oxides such as CaO. In addition, it is generally understood that as the ion exchange process proceeds and alkali ions penetrate more deeply into the glass, the maximum compressive stress achieved at the surface of the glass may decrease with time. However, glasses formed from glass compositions which are MgO-rich exhibit a lower reduction in compressive stress than glasses formed from glass compositions that are CaO-rich or rich in other alkaline earth oxides (i.e., glasses which are MgO-poor). Thus, MgO-rich glass compositions enable glasses which have higher compressive stress at the surface and greater depths of layer than glasses which are rich in other alkaline earth oxides.

In order to fully realize the benefits of MgO in the glass compositions described herein, it has been determined that the ratio of the concentration of CaO to the sum of the concentration of CaO and the concentration of MgO in mol. % (i.e., (CaO/(CaO+MgO)) should be minimized. Specifically, it has been determined that (CaO/(CaO+MgO)) should be less than or equal to 0.5. In some embodiments (CaO/(CaO+MgO)) is less than or equal to 0.3 or even less than or equal to 0.2. In some other embodiments (CaO/(CaO+MgO)) may even be less than or equal to 0.1.

Boron oxide ($B_2O_3$) is a flux which may be added to glass compositions to reduce the viscosity at a given temperature (e.g., the strain, anneal and softening temperatures) thereby improving the formability of the glass. However, it has been found that additions of boron significantly decrease the diffusivity of sodium and potassium ions in the glass composition which, in turn, adversely impacts the ion exchange performance of the resultant glass. In particular, it has been found that additions of boron significantly increase the time required to achieve a given depth of layer relative to glass compositions which are boron free. Accordingly, in some embodiments described herein, the amount of boron added to the glass composition is minimized in order to improve the ion exchange performance of the glass composition.

For example, it has been determined that the impact of boron on the ion exchange performance of a glass composition can be mitigated by controlling the ratio of the concentration of $B_2O_3$ to the difference between the total concentration of the alkali oxides (i.e., $R_2O$, where R is the alkali metals) and alumina (i.e., $B_2O_3$ (mol. %)/($R_2O$ (mol. %)-$Al_2O_3$ (mol. %)). In particular, it has been determined that when the ratio of $B_2O_3/(R_2O-Al_2O_3)$ is greater than or equal to about 0 and less than about 0.3 or even less than about 0.2, the diffusivities of alkali oxides in the glass compositions are not diminished and, as such, the ion exchange performance of the glass composition is maintained. Accordingly, in some embodiments, the ratio of $B_2O_3/(R_2O-Al_2O_3)$ is greater than 0 and less than or equal to 0.3. In some of these embodiments, the ratio of $B_2O_3/(R_2O-Al_2O_3)$ is greater than 0 and less than or equal to 0.2. In some embodiments, the ratio of $B_2O_3/(R_2O-Al_2O_3)$ is greater than 0 and less than or equal to 0.15 or even less than or equal to 0.1. In some other embodiments, the ratio of $B_2O_3/(R_2O-Al_2O_3)$ may be greater than 0 and less than or equal to 0.05. Maintaining the ratio $B_2O_3/(R_2O-Al_2O_3)$ to be less than or equal to 0.3 or even less than or equal to 0.2 permits the inclusion of $B_2O_3$ to lower the strain point, anneal point and softening point of the glass composition without the $B_2O_3$ adversely impacting the ion exchange performance of the glass.

In the embodiments described herein, the concentration of $B_2O_3$ in the glass composition is generally less than or equal to about 4 mol. %, less than or equal to about 3 mol. %, less than or equal to about 2 mol. %, or even less than or equal to 1 mol. %. For example, in embodiments where $B_2O_3$ is present in the glass composition, the concentration of $B_2O_3$ may be greater than about 0.01 mol. % and less than or equal to 4 mol. %. In some of these embodiments, the concentration of $B_2O_3$ may be greater than about 0.01 mol. % and less than or equal to 3 mol. % In some embodiments, the $B_2O_3$ may be present in an amount greater than or equal to about 0.01 mol. % and less than or equal to 2 mol. %, or even less than or equal to 1.5 mol. %. Alternatively, the $B_2O_3$ may be present in an amount greater than or equal to about 1 mol. % and less than or equal to 4 mol. %, greater than or equal to about 1 mol. % and less than or equal to 3 mol. % or even greater than or equal to about 1 mol. % and less than or equal to 2 mol. %. In some of these embodiments, the concentration of $B_2O_3$ may be greater than or equal to about 0.1 mol. % and less than or equal to 1.0 mol. %.

While in some embodiments the concentration of $B_2O_3$ in the glass composition is minimized to improve the forming properties of the glass without detracting from the ion exchange performance of the glass, in some other embodiments the glass compositions are free from boron and compounds of boron such as $B_2O_3$. Specifically, it has been determined that forming the glass composition without boron or compounds of boron improves the ion exchangeability of the glass compositions by reducing the process time and/or temperature required to achieve a specific value of compressive stress and/or depth of layer.

In some embodiments of the glass compositions described herein, the glass compositions are free from phosphorous and compounds containing phosphorous including, without limitation, $P_2O_5$. Specifically, it has been determined that formulating the glass composition without phosphorous or compounds of phosphorous increases the chemical durability of the glass composition.

In addition to the $SiO_2$, $Al_2O_3$, alkali oxides and alkaline earth oxides, the glass compositions described herein may optionally further comprise one or more fining agents such as, for example, $SnO_2$, $As_2O_3$, and/or $Cl^-$ (from NaCl or the like). When a fining agent is present in the glass composition, the fining agent may be present in an amount less than or equal to about 1 mol. % or even less than or equal to about 0.4 mol. %. For example, in some embodiments the glass composition may include $SnO_2$ as a fining agent. In these embodiments $SnO_2$ may be present in the glass composition in an amount greater than about 0 mol. % and less than or equal to about 1 mol. % or even an amount greater than or equal to about 0.01 mol. % and less than or equal to about 0.30 mol. %.

Moreover, the glass compositions described herein may comprise one or more additional metal oxides to further improve the chemical durability of the glass composition. For example, the glass composition may further include ZnO, $TiO_2$, or $ZrO_2$, each of which further improves the resistance of the glass composition to chemical attack. In these embodiments, the additional metal oxide may be present in an amount which is greater than or equal to about 0 mol. % and less than or equal to about 2 mol. %. For example, when the additional metal oxide is ZnO, the ZnO may be present in an amount greater than or equal to 1 mol. % and less than or equal to about 2 mol. %. When the additional metal oxide is $ZrO_2$ or $TiO_2$, the $ZrO_2$ or $TiO_2$ may be present in an amount less than or equal to about 1 mol. %.

Based on the foregoing, it should be understood that, in a first exemplary embodiment, a glass composition may include: $SiO_2$ in a concentration greater than about 70 mol. % and Y mol. % alkali oxide. The alkali oxide may include $Na_2O$ in an amount greater than about 8 mol. %. The glass composition may be free of boron and compounds of boron. The concentration of $SiO_2$ in this glass composition may be greater than or equal to about 72 mol. %, greater than 73 mol. % or even greater than 74 mol. %. The glass composition of this first exemplary embodiment may be free from phosphorous and compounds of phosphorous. The glass composition may also include X mol. % $Al_2O_3$. When $Al_2O_3$ is included, the ratio of Y:X may be greater than 1. The concentration of $Al_2O_3$ may be greater than or equal to about 2 mol. % and less than or equal to about 10 mol. %.

The glass composition of this first exemplary embodiment may also include alkaline earth oxide in an amount from about 3 mol. % to about 13 mol. %. The alkaline earth oxide may include MgO and CaO. The CaO may be present in an amount greater than or equal to about 0.1 mol. % and less than or equal to about 1.0 mol. %. A ratio (CaO (mol. %)/(CaO (mol. %)+MgO (mol. %))) may be less than or equal to 0.5.

In a second exemplary embodiment, a glass composition may include: greater than about 68 mol. % $SiO_2$; X mol. % $Al_2O_3$; Y mol. % alkali oxide; and $B_2O_3$. The alkali oxide may include $Na_2O$ in an amount greater than about 8 mol %. A ratio ($B_2O_3$ (mol. %)/(Y mol. %–X mol. %) may be greater than 0 and less than 0.3. The concentration of $SiO_2$ in this glass composition may be greater than or equal to about 72 mol. %, greater than 73 mol. % or even greater than 74 mol. %. The concentration of $Al_2O_3$ may be greater than or equal to about 2 mol. % and less than or equal to about 10 mol. %. In this second exemplary embodiment, the ratio of Y:X may be greater than 1. When the ratio of Y:X is greater than 1, an upper bound of the ratio of Y:X may be less than or equal to 2. The glass composition of this first exemplary embodiment may be free from phosphorous and compounds of phosphorous.

The glass composition of this second exemplary embodiment may also include alkaline earth oxide. The alkaline earth oxide may include MgO and CaO. The CaO may be present in an amount greater than or equal to about 0.1 mol. % and less than or equal to about 1.0 mol. %. A ratio (CaO (mol. %)/(CaO (mol. %)+MgO (mol. %))) may be less than or equal to 0.5.

The concentration of $B_2O_3$ in this second exemplary embodiment may be greater than or equal to about 0.01 mol. % and less than or equal to about 4 mol. %.

In a third exemplary embodiment, a glass article may have a type HgB1 hydrolytic resistance according to ISO 719. The glass article may include greater than about 8 mol. % $Na_2O$ and less than about 4 mol. % $B_2O_3$. The glass article may further comprise X mol. % $Al_2O_3$ and Y mol. % alkali oxide. The ratio ($B_2O_3$ (mol. %)/(Y mol. %–X mol. %) may be greater than 0 and less than 0.3. The glass article of this third exemplary embodiment may further include a compressive stress layer having a surface compressive stress greater than or equal to about 250 MPa. The glass article may also have at least a class S3 acid resistance according to DIN 12116; at least a class A2 base resistance according to ISO 695; and a type HgA1 hydrolytic resistance according to ISO 720.

In a fourth exemplary embodiment, a glass pharmaceutical package may include $SiO_2$ in an amount greater than about 70 mol. %; X mol. % $Al_2O_3$; and Y mol. % alkali oxide. The alkali oxide may include $Na_2O$ in an amount greater than about 8 mol. %. A ratio of a concentration of $B_2O_3$ (mol. %) in the glass pharmaceutical package to (Y mol. %–X mol. %) may be less than 0.3. The glass pharmaceutical package may also have a type HGB1 hydrolytic resistance according to ISO 719. The concentration of $SiO_2$ in the glass pharmaceutical package of this fourth exemplary embodiment may be greater than or equal to 72 mol. % and less than or equal to about 78 mol. % or even greater than 74 mol. % and less than or equal to about 78 mol. %. The concentration of $Al_2O_3$ in the glass pharmaceutical may be greater than or equal to about 4 mol. % and less than or equal to about 8 mol. %. A ratio of Y:X may be greater than 1 and less than 2.

The glass pharmaceutical package of this fourth exemplary embodiment may also include alkaline earth oxide in an amount from about 4 mol. % to about 8 mol. %. The alkaline earth oxide may include MgO and CaO. The CaO may be present in an amount greater than or equal to about 0.2 mol. % and less than or equal to about 0.7 mol. %. A ratio (CaO (mol. %)/(CaO (mol. %)+MgO (mol. %))) may be less than or equal to 0.5. The glass pharmaceutical package of this fourth exemplary embodiment may have a type HGA1 hydrolytic resistance according to ISO 720.

In a fifth exemplary embodiment, a glass composition may include from about 70 mol. % to about 80 mol. % $SiO_2$; from about 3 mol. % to about 13 mol. % alkaline earth oxide; X mol. % $Al_2O_3$; and Y mol. % alkali oxide. The alkali oxide may include $Na_2O$ in an amount greater than about 8 mol. %. A ratio of Y:X may be greater than 1. The glass composition may be free of boron and compounds of boron.

In a sixth exemplary embodiment, a glass composition may include from about 68 mol. % to about 80 mol. % $SiO_2$; from about 3 mol. % to about 13 mol. % alkaline earth oxide; X mol. % $Al_2O_3$; and Y mol. % alkali oxide. The alkali oxide may include $Na_2O$ in an amount greater than about 8 mol. %. The glass composition of this sixth exemplary embodiment may also include $B_2O_3$. A ratio ($B_2O_3$ (mol. %)/(Y mol. %–X mol. %) may be greater than 0 and less than 0.3. A ratio of Y:X may be greater than 1.

In a seventh exemplary embodiment, a glass composition may include from about 70 mol. % to about 80 mol. % $SiO_2$; from about 3 mol. % to about 13 mol. % alkaline earth oxide; X mol. % $Al_2O_3$; and Y mol. % alkali oxide. The amount of $Al_2O_3$ in the glass composition may be greater than or equal to about 2 mol. % and less than or equal to about 10 mol. %. The alkaline earth oxide may include CaO in an amount greater than or equal to about 0.1 mol. % and less than or equal to about 1.0 mol. %. The alkali oxide may include from about 0.01 mol. % to about 1.0 mol. % $K_2O$. A ratio of Y:X may be greater than 1. The glass composition may be free of boron and compounds of boron. The glass composition may be amenable to strengthening by ion exchange.

In a seventh exemplary embodiment, a glass composition may include $SiO_2$ in an amount greater than about 70 mol. % and less than or equal to about 80 mol. %; X mol. % $Al_2O_3$; and Y mol. % alkali oxide. The alkali oxide may include $Na_2O$ in an amount greater than about 8 mol. %. A ratio of a concentration of $B_2O_3$ (mol. %) in the glass pharmaceutical package to (Y mol. %–X mol. %) may be less than 0.3. A ratio of Y:X may be greater than 1.

In an eighth exemplary embodiment, a glass composition may include from about 72 mol. % to about 78 mol. % $SiO_2$; from about 4 mol. % to about 8 mol. % alkaline earth oxide; X mol. % $Al_2O_3$, wherein X is greater than or equal to about 4 mol. % and less than or equal to about 8 mol. %; and Y mol. % alkali oxide, wherein the alkali oxide comprises $Na_2O$ in an amount greater than or equal to about 9 mol. % and less than or equal to about 15 mol. %. A ratio of a concentration of $B_2O_3$ (mol. %) in the glass pharmaceutical package to (Y mol. %–X mol. %) is less than 0.3. A ratio of Y:X may be greater than 1.

In a ninth exemplary embodiment, a pharmaceutical package for containing a pharmaceutical composition may include from about 70 mol. % to about 78 mol. % $SiO_2$; from about 3 mol. % to about 13 mol. % alkaline earth oxide; X mol. % $Al_2O_3$, wherein X is greater than or equal to 2 mol. % and less than or equal to about 10 mol. %; and Y mol. % alkali oxide, wherein the alkali oxide comprises $Na_2O$ in an amount greater than about 8 mol. %. The alkaline earth oxide may include CaO in an amount less than or equal to about 6.0 mol. %. A ratio of Y:X may be greater than about 1. The package may be free of boron and compounds of boron and may include a compressive stress layer with a compressive stress greater than or equal to about 250 MPa and a depth of layer greater than or equal to about 10 μm.

In a tenth exemplary embodiment, a glass article may be formed from a glass composition comprising from about 70 mol. % to about 78 mol. % $SiO_2$; alkaline earth oxide, wherein the alkaline earth oxide comprises MgO and CaO and a ratio (CaO (mol. %)/(CaO (mol. %)+MgO (mol. %))) is less than or equal to 0.5; X mol. % $Al_2O_3$, wherein X is from about 2 mol. % to about 10 mol. %; and Y mol. % alkali oxide, wherein the alkali oxide comprises $Na_2O$ in an amount greater than about 8 mol. % and a ratio of Y:X is greater than 1. The glass article may be ion exchange strengthened with a compressive stress greater than or equal to 250 MPa and a depth of layer greater than or equal to 10 μm. The glass article may have a type HgA1 hydrolytic resistance according to ISO 720.

As noted above, the presence of alkali oxides in the glass composition facilitates chemically strengthening the glass by ion exchange. Specifically, alkali ions, such as potassium ions, sodium ions and the like, are sufficiently mobile in the glass to facilitate ion exchange. In some embodiments, the glass composition is ion exchangeable to form a compressive stress layer having a depth of layer greater than or equal to 10 μm. In some embodiments, the depth of layer may be greater than or equal to about 25 μm or even greater than or equal to about 50 μm. In some other embodiments, the depth of the layer may be greater than or equal to 75 μm or even greater than or equal to 100 μm. In still other embodiments, the depth of layer may be greater than or equal to 10 μm and less than or equal to about 100 μm. The associated surface compressive stress may be greater than or equal to about 250 MPa, greater than or equal to 300 MPa or even greater than or equal to about 350 MPa after the glass composition is treated in a salt bath of 100% molten $KNO_3$ at a temperature of 350° C. to 500° C. for a time period of less than about 30 hours or even about less than 20 hours.

The glass articles formed from the glass compositions described herein may have a hydrolytic resistance of HGB2 or even HGB1 under ISO 719 and/or a hydrolytic resistance of HGA2 or even HGA1 under ISO 720 (as described further herein) in addition to having improved mechanical characteristics due to ion exchange strengthening. In some embodiments described herein the glass articles may have compressive stresses which extend from the surface into the glass article to a depth of layer greater than or equal to 25 μm or even greater than or equal to 35 μm. In some embodiments, the depth of layer may be greater than or equal to 40 μm or even greater than or equal to 50 μm. The surface compressive stress of the glass article may be greater than or equal to 250 MPa, greater than or equal to 350 MPa, or even greater than or equal to 400 MPa. The glass compositions described herein facilitate achieving the aforementioned depths of layer and surface compressive stresses more rapidly and/or at lower temperatures than conventional glass compositions due to the enhanced alkali ion diffusivity of the glass compositions as described hereinabove. For example, the depths of layer (i.e., greater than or equal to 25 μm) and the compressive stresses (i.e., greater than or equal to 250 MPa) may be achieved by ion exchanging the glass article in a molten salt bath of 100% $KNO_3$ (or a mixed salt bath of $KNO_3$ and $NaNO_3$) for a time period of less than or equal to 5 hours or even less than or equal to 4.5 hours. In some embodiments, these depths of layer and compressive stresses may be achieved by ion exchanging the glass article in a molten salt bath of 100% $KNO_3$ (or a mixed salt bath of $KNO_3$ and $NaNO_3$) for a time period of less than or equal to 4 hours or even less than or equal to 3.5 hours. Moreover, these depths of layers and compressive stresses may be achieved by ion exchanging the glass articles in a molten salt bath of 100% KNO3 (or a mixed salt bath of $KNO_3$ and $NaNO_3$) at a temperature less than or equal to 500° C. or even less than or equal to 450° C. In some embodiments, these depths of layers and compressive stresses may be achieved by ion exchanging the glass articles in a molten salt bath of 100% KNO3 (or a mixed salt bath of $KNO_3$ and $NaNO_3$) at a temperature less than or equal to 400° C. or even less than or equal to 350° C.

These improved ion exchange characteristics can be achieved when the glass composition has a threshold diffusivity of greater than about 16 μm²/hr or even greater than or equal to 20 μm²/hr at 450° C. In some embodiments, the threshold diffusivity may be greater than or equal to about 25 m²/hr or even 30 m²/hr at 450° C. In some other embodiments, the threshold diffusivity may be greater than or equal to about 35 μm²/hr or even 40 μm²/hr at 450° C. In still other embodiments, the threshold diffusivity may be greater than or equal to about 45 m²/hr or even 50 m²/hr at 450° C.

The glass compositions described herein may generally have a strain point greater than or equal to about 525° C. and less than or equal to about 650° C. The glasses may also have an anneal point greater than or equal to about 560° C. and less than or equal to about 725° C. and a softening point greater than or equal to about 750° C. and less than or equal to about 960° C.

In the embodiments described herein the glass compositions have a CTE of less than about $70 \times 10^{-7} K^{-1}$ or even less than about $60 \times 10^{-7} K^{-1}$. These lower CTE values improve the survivability of the glass to thermal cycling or thermal stress conditions relative to glass compositions with higher CTEs.

Further, as noted hereinabove, the glass compositions are chemically durable and resistant to degradation as determined by the DIN 12116 standard, the ISO 695 standard, and the ISO 720 standard.

Specifically, the DIN 12116 standard is a measure of the resistance of the glass to decomposition when placed in an acidic solution. In brief, the DIN 12116 standard utilizes a polished glass sample of a known surface area which is weighed and then positioned in contact with a proportional amount of boiling 6M hydrochloric acid for 6 hours. The sample is then removed from the solution, dried and weighed again. The glass mass lost during exposure to the acidic solution is a measure of the acid durability of the sample with smaller numbers indicative of greater durability. The results of the test are reported in units of half-mass per surface area, specifically mg/dm$^2$. The DIN 12116 standard is broken into individual classes. Class S1 indicates weight losses of up to 0.7 mg/dm$^2$; Class S2 indicates weight losses from 0.7 mg/dm$^2$ up to 1.5 mg/dm$^2$; Class S3 indicates weight losses from 1.5 mg/dm$^2$ up to 15 mg/dm$^2$; and Class S4 indicates weight losses of more than 15 mg/dm$^2$.

The ISO 695 standard is a measure of the resistance of the glass to decomposition when placed in a basic solution. In brief, the ISO 695 standard utilizes a polished glass sample which is weighed and then placed in a solution of boiling 1M NaOH+0.5M Na$_2$CO$_3$ for 3 hours. The sample is then removed from the solution, dried and weighed again. The glass mass lost during exposure to the basic solution is a measure of the base durability of the sample with smaller numbers indicative of greater durability. As with the DIN 12116 standard, the results of the ISO 695 standard are reported in units of mass per surface area, specifically mg/dm$^2$. The ISO 695 standard is broken into individual classes. Class A1 indicates weight losses of up to 75 mg/dm$^2$; Class A2 indicates weight losses from 75 mg/dm$^2$ up to 175 mg/dm$^2$; and Class A3 indicates weight losses of more than 175 mg/dm$^2$.

The ISO 720 standard is a measure of the resistance of the glass to degradation in purified, CO$_2$-free water. In brief, the ISO 720 standard protocol utilizes crushed glass grains which are placed in contact with the purified, CO$_2$-free water under autoclave conditions (121° C., 2 atm) for 30 minutes. The solution is then titrated colorimetrically with dilute HCl to neutral pH. The amount of HCl required to titrate to a neutral solution is then converted to an equivalent of Na$_2$O extracted from the glass and reported in µg Na$_2$O per weight of glass with smaller values indicative of greater durability. The ISO 720 standard is broken into individual types. Type HGA1 is indicative of up to 62 µg extracted equivalent of Na$_2$O per gram of glass tested; Type HGA2 is indicative of more than 62 µg and up to 527 µg extracted equivalent of Na$_2$O per gram of glass tested; and Type HGA3 is indicative of more than 527 µg and up to 930 µg extracted equivalent of Na$_2$O per gram of glass tested.

The ISO 719 standard is a measure of the resistance of the glass to degradation in purified, CO$_2$-free water. In brief, the ISO 719 standard protocol utilizes crushed glass grains which are placed in contact with the purified, CO$_2$-free water at a temperature of 98° C. at 1 atmosphere for 30 minutes. The solution is then titrated colorimetrically with dilute HCl to neutral pH. The amount of HCl required to titrate to a neutral solution is then converted to an equivalent of Na$_2$O extracted from the glass and reported in µg Na$_2$O per weight of glass with smaller values indicative of greater durability. The ISO 719 standard is broken into individual types. The ISO 719 standard is broken into individual types. Type HGB1 is indicative of up to 31 µg extracted equivalent of Na$_2$O; Type HGB2 is indicative of more than 31 µg and up to 62 µg extracted equivalent of Na$_2$O; Type HGB3 is indicative of more than 62 µg and up to 264 µg extracted equivalent of Na$_2$O; Type HGB4 is indicative of more than 264 µg and up to 620 µg extracted equivalent of Na$_2$O; and Type HGB5 is indicative of more than 620 µg and up to 1085 µg extracted equivalent of Na$_2$O. The glass compositions described herein have an ISO 719 hydrolytic resistance of type HGB2 or better with some embodiments having a type HGB1 hydrolytic resistance.

The glass compositions described herein have an acid resistance of at least class S3 according to DIN 12116 both before and after ion exchange strengthening with some embodiments having an acid resistance of at least class S2 or even class 51 following ion exchange strengthening. In some other embodiments, the glass compositions may have an acid resistance of at least class S2 both before and after ion exchange strengthening with some embodiments having an acid resistance of class 51 following ion exchange strengthening. Further, the glass compositions described herein have a base resistance according to ISO 695 of at least class A2 before and after ion exchange strengthening with some embodiments having a class A1 base resistance at least after ion exchange strengthening. The glass compositions described herein also have an ISO 720 type HGA2 hydrolytic resistance both before and after ion exchange strengthening with some embodiments having a type HGA1 hydrolytic resistance after ion exchange strengthening and some other embodiments having a type HGA1 hydrolytic resistance both before and after ion exchange strengthening. The glass compositions described herein have an ISO 719 hydrolytic resistance of type HGB2 or better with some embodiments having a type HGB1 hydrolytic resistance. It should be understood that, when referring to the above referenced classifications according to DIN 12116, ISO 695, ISO 720 and ISO 719, a glass composition or glass article which has "at least" a specified classification means that the performance of the glass composition is as good as or better than the specified classification. For example, a glass article which has a DIN 12116 acid resistance of "at least class S2" may have a DIN 12116 classification of either S1 or S2.

The glass compositions described herein are formed by mixing a batch of glass raw materials (e.g., powders of SiO$_2$, Al$_2$O$_3$, alkali oxides, alkaline earth oxides and the like) such that the batch of glass raw materials has the desired composition. Thereafter, the batch of glass raw materials is heated to form a molten glass composition which is subsequently cooled and solidified to form the glass composition. During solidification (i.e., when the glass composition is plastically deformable) the glass composition may be shaped using standard forming techniques to shape the glass composition into a desired final form. Alternatively, the glass article may be shaped into a stock form, such as a sheet, tube or the like, and subsequently reheated and formed into the desired final form.

Pharmaceutical Containers

In view of the chemical durability of the glass composition of the present invention, the glass compositions described herein are particularly well suited for use in designing pharmaceutical containers for storing, maintaining and/or delivering pharmaceutical compositions, such as liquids, solutions, powders, e.g., lyophilized powders, solids and the like. As used herein, the term "pharmaceutical container" refers to a composition designed to store, maintain and/or deliver a pharmaceutical composition. The pharmaceutical containers, as described herein, are formed, at least in part, of the delamination resistant glass compositions described above. Pharmaceutical containers of the present invention include, but are not limited to, Vacutainers™, cartridges, syringes, ampoules, bottles, flasks, phials, tubes, beakers, vials, injection pens or the like. In a particular embodiment, the pharmaceutical container is a vial. In a particular embodiment, the pharmaceutical container is an ampoule. In a particular embodiment, the pharmaceutical container is an injection pen. In a particular embodiment, the pharmaceutical container is a tube. In a particular embodiment, the pharmaceutical container is a bottle. In a particular embodiment, the pharmaceutical container is a syringe.

Moreover, the ability to chemically strengthen the glass compositions through ion exchange can be utilized to improve the mechanical durability of pharmaceutical containers formed from the glass composition. Accordingly, it should be understood that, in at least one embodiment, the glass compositions are incorporated in a pharmaceutical container in order to improve the chemical durability and/or the mechanical durability of the pharmaceutical container.

Pharmaceutical Compositions

In various embodiments, the pharmaceutical container further includes a pharmaceutical composition comprising an active pharmaceutical ingredient (API). As used herein, the term "pharmaceutical composition" refers to a composition comprising an active pharmaceutical ingredient to be delivered to a subject, for example, for therapeutic, prophylactic, diagnostic, preventative or prognostic effect. In certain embodiments, the pharmaceutical composition comprises the active pharmaceutical ingredient and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active pharmaceuical agent.

As used herein, the term "active pharmaceutical ingredient" or "API" refers a substance in a pharmaceutical composition that provides a desired effect, for example, a therapeutic, prophylactic, diagnostic, preventative or prognostic effect. In various embodiments, the active pharmaceutical ingredient can be any of a variety of substances known in the art, for example, a small molecule, a polypeptide mimetic, a biologic, an antisense RNA, a small interfering RNA (siRNA), etc.

For example, in a particular embodiment, the active pharmaceutical ingredient may be a small molecule. As used herein, the term "small molecule" includes any chemical or other moiety, other than polypeptides and nucleic acids, that can act to affect biological processes. Small molecules can include any number of therapeutic agents presently known and used, or that can be synthesized from a library of such molecules for the purpose of screening for biological function(s). Small molecules are distinguished from macromolecules by size. The small molecules of the present invention usually have a molecular weight less than about 5,000 daltons (Da), preferably less than about 2,500 Da, more preferably less than 1,000 Da, most preferably less than about 500 Da.

Small molecules include, without limitation, organic compounds, peptidomimetics and conjugates thereof. As used herein, the term "organic compound" refers to any carbon-based compound other than macromolecules such as nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds.

In another embodiment, the active pharmaceutical ingredient may be a polypeptide mimetic ("peptidomimetic"). As used herein, the term "polypeptide mimetic" is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides, and peptoids.

In other embodiments, the active pharmaceutical ingredient may be a biologic. As used herein, the term "biologic" includes products created by biologic processes instead of by chemical synthesis. Non-limiting examples of a "biologic" include proteins, antibodies, antibody like molecules, vaccines, blood, blood components, and partially purified products from tissues.

The terms "peptide," "polypeptide," and "protein" are used interchangeably herein. In the present invention, these terms mean a linked sequence of amino acids, which may be natural, synthetic, or a modification or combination of natural and synthetic. The term includes antibodies, antibody mimetics, domain antibodies, lipocalins, and targeted proteases. The term also includes vaccines containing a peptide or peptide fragment intended to raise antibodies against the peptide or peptide fragment.

"Antibody" as used herein includes an antibody of classes IgG, IgM, IgA, IgD, or IgE, or fragments or derivatives thereof, including Fab, F(ab')2, Fd, and single chain antibodies, diabodies, bispecific antibodies, and bifunctional antibodies. The antibody may be a monoclonal antibody, polyclonal antibody, affinity purified antibody, or mixtures thereof, which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody.

Other antibody-like molecules are also within the scope of the present invention. Such antibody-like molecules include, e.g., receptor traps (such as entanercept), antibody mimetics (such as adnectins, fibronectin based "addressable" therapeutic binding molecules from, e.g., Compound Therapeutics, Inc.), domain antibodies (the smallest functional fragment of a naturally occurring single-domain antibody (such as, e.g., nanobodies; see, e.g., Cortez-Retamozo et al., Cancer Res. 2004 Apr. 15; 64 (8):2853-7)).

Suitable antibody mimetics generally can be used as surrogates for the antibodies and antibody fragments described herein. Such antibody mimetics may be associated with advantageous properties (e.g., they may be water soluble, resistant to proteolysis, and/or be nonimmunogenic). For example, peptides comprising a synthetic beta-loop structure that mimics the second complementarity-determining region (CDR) of monoclonal antibodies have been proposed and generated. See, e.g., Saragovi et al., Science. Aug. 16, 1991; 253 (5021):792-5. Peptide antibody mimetics also have been generated by use of peptide mapping to determine "active" antigen recognition residues, molecular modeling, and a molecular dynamics trajectory analysis, so as to design a peptide mimic containing antigen contact residues from multiple CDRs. See, e.g., Cassett et al., Biochem Biophys Res Commun. Jul. 18, 2003; 307 (1):198-205. Additional discussion of related principles, methods, etc., that may be applicable in the context of this invention are provided in, e.g., Fassina, Immunomethods. October 1994; 5 (2):121-9.

In various embodiments, the active pharmaceutical ingredient may have any of a variety of activities selected from the group consisting of anti-rheumatics, anti-neoplastic, vaccines, anti-diabetics, haematologicals, muscle relaxant, immunostimulants, anti-coagulants, bone calcium regulators, sera and gammaglobulins, anti-fibrinolytics, MS therapies, anti-anaemics, cytostatics, interferons, anti-metabolites, radiopharmaceuticals, anti-psychotics, anti-bacterials, immunosuppressants, cytotoxic antibiotics, cerebral & peripheral vasotherapeutics, nootropics, CNS drugs, dermatologicals, angiotensin antagonists, anti-spasmodics, anti-cholinergics, interferons, anti-psoriasis agents, anti-hyperlipidaemics, cardiac therapies, alkylating agents, bronchodilators, anti-coagulants, anti-inflammatories, growth hormones, and diagnostic imaging agents.

In various embodiments, the pharmaceutical composition may be selected from the group consisting of Neupogen® (Filgrastim), Neulasta® (pegfilgrastim), Epogen® (epoetin alfa) and Enbrel® (etanercept).

In a particular embodiment, the pharmaceutical composition comprises filgrastim. In a particular embodiment, the active pharmaceutical ingredient comprises recombinant human granulocyte colony-stimulating factor, or an analog thereof. Filgrastim (NEUPOGEN®) is a form of recombinant human granulocyte colony-stimulating factor (G-CSF). Colony-stimulating factors are glycoproteins which act on hematopoietic cells by binding to specific cell surface receptors and stimulating proliferation, differentiation, commitment, and some end-cell functional activation. Filgrastim is presently indicated to decrease the incidence of infection, as manifested by febrile neutropenia, in patients with non-myeloid malignancies receiving myelosuppressive anti-cancer drugs associated with a clinically significant incidence of febrile neutropenia.

Filgrastim is a 175 amino acid protein and has a molecular weight of 18,800 daltons. The protein has an amino acid sequence that is identical to the natural sequence predicted from human DNA sequence analysis, except for the addition of an N-terminal methionine necessary for expression in $E$ $coli$. Because NEUPOGEN® NEUPOGEN® is produced in $E\ coli$, the product is nonglycosylated and thus differs from G-CSF isolated from a human cell.

Filgrastim is a sterile, clear, colorless, preservative-free liquid for parenteral administration containing filgrastim at a specific activity of $1.0\pm0.6\times10^8$ U/mg (as measured by a cell mitogenesis assay). Filgrastim is currently supplied in single-use vials and prefilled syringes. The single-use vials contain either 300 mcg or 480 mcg filgrastim at a fill volume of 1.0 mL or 1.6 mL, respectively. The single-use prefilled syringes contain either 300 mcg or 480 mcg filgrastim at a fill volume of 0.5 mL or 0.8 mL, respectively.

In a particular embodiment, the pharmaceutical composition comprises Pegfilgrastim. In a particular embodiment, the active pharmaceutical ingredient comprises PEGylated recombinant human granulocyte colony-stimulating factor, or an analog thereof. Pegfilgrastim (NEULASTA®; NEULASTIM®), a PEGylated form of the recombinant human granulocyte colony-stimulating factor (G-CSF) analog, filgrastim, is a leukocyte growth factor that is presently indicated to decrease the incidence of infection, as manifested by febrile neutropenia, in patients with non-myeloid malignancies receiving myelosuppressive anti-cancer drugs associated with a clinically significant incidence of febrile neutropenia.

Pegfilgrastim, having an average molecular weight of approximately 39 kD, is a colony-stimulating factor that acts on hematopoietic cells by binding to specific cell surface receptors, thereby stimulating proliferation, differentiation, commitment, and end cell functional activation. Pegfilgrastim is a covalent conjugate of recombinant methionyl human G-CSF (filgrastim) and monomethoxypolyethylene glycol. Filgrastim is a water-soluble 175 amino acid protein with a molecular weight of approximately 19 kD. Filgrastim is obtained from the bacterial fermentation of a strain of $E.\ coli$ transformed with a genetically engineered plasmid containing the human G-CSF gene. To produce pegfilgrastim, a 20 kD monomethoxypolyethylene glycol molecule is covalently bound to the N-terminal methionyl residue of filgrastim.

Pegfilgrastim is currently supplied as a single use prefilled syringe for subcutaneous injection and is formulated in a sterile, clear, colorless, preservative-free solution (pH 4.0) containing acetate, polysorbate 20, sodium, and sorbitol in Water for Injection, USP.

In particular embodiments, the pharmaceutical composition comprises epoetin alfa. In a particular embodiment, the active pharmaceutical ingredient comprises recombinant human erythropoietin or an analog thereof. Epoetin alpha (EPOGEN®) is a form of recombinant human erythropoietin. Epoetin alpha is presently indicated for treatment of anemia due to chronic kidney disease (CKD) in patients on dialysis and not on dialysis, in zidovudine in HIV-infected patients, to counter the effects of concomitant myelosuppressive chemotherapy, and reduction of allogeneic RBC transfusions in patients undergoing elective, noncardiac, nonvascular surgery.

Epoetin alpha is a 165-amino acid erythropoiesis-stimulating glycoprotein manufactured by recombinant DNA technology that has a molecular weight of approximately 30,400 daltons and is produced by mammalian cells into which the human erythropoietin gene has been introduced. The product contains the identical amino acid sequence of isolated natural erythropoietin.

Epoetin alpha is presently formulated as a sterile, colorless liquid in vials in multiple formulations. Single-dose vials, formulated with an isotonic sodium chloride/sodium citrate-buffered solution, are supplied in multiple strengths. Each 1 mL vial contains 2000, 3000, 4000, or 10,000 Units of epoetin alfa, Albumin (Human) (2.5 mg), citric acid (0.06 mg), sodium chloride (5.9 mg), and sodium citrate (5.8 mg) in Water for Injection, USP (pH 6.9±0.3). Single-dose 1 mL vials formulated with an isotonic sodium chloride/sodium phosphate buffer contain 40,000 Units of epoetin alfa albumin (human) (2.5 mg), citric acid (0.0068 mg), sodium chloride (5.8 mg), sodium citrate (0.7 mg), sodium phosphate dibasic anhydrate (1.8 mg), and sodium phosphate monobasic monohydrate (1.2 mg) in Water for Injection, USP (pH 6.9±0.3). Multidose, 2 mL vials contain 10,000 Units epoetin alfa, albumin (human) (2.5 mg), benzyl alcohol (1%), sodium chloride (8.2 mg), and sodium citrate (1.3 mg) per 1 mL Water for Injection, USP (pH 6.1±0.3). Multidose 1 mL vials contain 20,000 Units epoetin alfa, albumin (human) (2.5 mg), benzyl alcohol (1%), sodium chloride (8.2 mg), citric acid (0.11 mg), and sodium citrate (1.3 mg), per 1 mL in Water for Injection, USP (pH 6.1±0.3).

In a particular embodiment, the pharmaceutical composition comprises Etanercept. Etanercept (Enbrel®) is a dimeric fusion protein indicated for the treatment of Rheumatoid Arthritis (RA), Polyarticular Juvenile Idiopathic Arthritis (JIA) in patients aged 2 years or older, Psoriatic Arthritis (PsA), Ankylosing Spondylitis (AS), and Plaque Psoriasis (PsO).

Etanercept, consisting of 934 amino acids and having an apparent molecular weight of approximately 150 kD, inhibits binding of TNF-alpha and TNF-beta (lymphotoxin alpha [LT-alpha]) to cell surface tumor necrosis factor receptors (TN-FRs), rendering TNF biologically inactive. Etanercept consists of the extracellular ligand-binding portion of the human 75 kD (p75) tumor necrosis factor receptor (TNFR) linked to the Fc portion of human IgG1.

Etanercept can modulate biological responses that are induced or regulated by TNF, including expression of adhesion molecules responsible for leukocyte migration (eg, E-selectin, and to a lesser extent, intercellular adhesion molecule-1 [ICAM-1]), serum levels of cytokines (eg, IL-6), and serum levels of matrix metalloproteinase-3 (MMP-3 or stromelysin). The Fc component of etanercept contains the CH2 domain, the CH3 domain and hinge region, but not the CH1 domain of IgG1. Etanercept is produced by recombinant DNA technology in a Chinese hamster ovary (CHO) mammalian cell expression system.

Etanercept is supplied in a single-use prefilled syringe or autoinjector for subcutaneous injection and is formulated with sucrose, sodium chloride, L-arginine hydrochloride, and sodium phosphate to pH 6.3±0.2. Etanercept is also supplied in a multiple-use vial as a lyophilized powder with mannitol, sucrose, and tromethamine, which can be reconstituted using Sterile Bacteriostatic Water for Injection, USP (0.9% benzyl alcohol) to pH 7.4±0.3.

Degradation and Stability of Pharmaceutical Compositions

According to the present invention, delamination resistant pharmaceutical containers comprising a glass composition provide for improved resistance to degradation of, improved stability of, improved resistance to inactivation of, and improved maintenance of levels of a pharmaceutical composition having at least one active pharmaceutical ingredient, for example, NEUPOGEN® (filgrastim), NEULASTA® (pegfilgrastim), EPOGEN® (epoetin alfa) or ENBREL® (etanercept).

In one embodiment of the present invention, the delamination resistant pharmaceutical containers provide improved stability to pharmaceutical compositions contained therein, for example, NEUPOGEN® (filgrastim), NEULASTA® (pegfilgrastim), EPOGEN® (epoetin alfa) or ENBREL® (etanercept). As used herein, the term "stability" refers to the ability of an active pharmaceutical ingredient to essentially retain its physical, chemical and conformational identity and integrity upon storage in the pharmaceutical containers of the invention. Stability is associated with the ability of an active pharmaceutical ingredient to retain its potency and efficacy over a period of time. Instability of an active pharmaceutical ingredient may be associated with, for example, chemical or physical degradation, fragmentation, conformational change, increased toxicity, aggregation (e.g., to form higher order polymers), deglycosylation, modification of glycosylation, oxidation, hydrolysis, or any other structural, chemical or physical modification. Such physical, chemical and/or conformational changes often result in reduced activity or inactivation of the active pharmaceutical ingredient, for example, such that at least one biological activity of the active pharmaceutical ingredient is reduced or eliminated. Alternatively or in addition, such physical, chemical and/or conformational changes often result in the formation of structures toxic to the subject to whom the pharmaceutical composition is administered.

The pharmaceutical containers of the present invention maintain stability of the pharmaceutical compositions, in part, by minimizing or eliminating delamination of the glass composition which forms, at least in part, the pharmaceutical container. In addition, the pharmaceutical containers of the present invention maintain stability of the pharmaceutical compositions, in part, by reducing or preventing the interaction of the active pharmaceutical ingredient with the pharmaceutical container and/or delaminated particles resulting therefrom. By minimizing or eliminating delamination and, further, by reducing or preventing interaction, the pharmaceutical containers thereby reduce or prevent the destabilization of the active pharmaceutical ingredient as found in, for example, NEUPOGEN® (filgrastim), NEULASTA® (pegfilgrastim), EPOGEN® (epoetin alfa) or ENBREL® (etanercept).

The pharmaceutical containers of the present invention provide the additional advantage of preventing loss of active pharmaceutical ingredients. For example, by reducing or preventing the interaction of and, thus, the adherence of, the active pharmaceutical ingredient with the pharmaceutical container and/or delaminated particles resulting therefrom, the level of active pharmaceutical ingredient available for administration to a subject is maintained, as found in, for example, NEUPOGEN® (filgrastim), NEULASTA® (pegfilgrastim), EPOGEN® (epoetin alfa) or ENBREL® (etanercept).

In one embodiment of the present invention, the pharmaceutical composition has a high pH. According to the present invention, it has been discovered that high pHs serve to increase delamination of glass compositions. Accordingly, the pharmaceutical containers of the present invention are particularly suitable for storing and maintaining pharmaceutical compositions having a high pH, for example, pharmaceutical compositions having a pH between about 7 and about 11, between about 7 and about 10, between about 7 and about 9, or between about 7 and about 8.

In additional embodiments, the pharmaceutical containers of the present invention are particularly suitable for storing and maintaining pharmaceutical compositions having phosphate or citrate based buffers. According to the present invention, it has been discovered that phosphate or citrate based buffers serve to increase delamination of glass compositions. According in particular embodiments, the pharmaceutical composition includes a buffer comprising a salt of citrate, e.g., sodium citrate, or SSC. In other embodiments, the pharmaceutical composition includes a buffer comprising a salt of phosphate, e.g., mono or disodium phosphate.

In additional embodiments, the pharmaceutical containers of the present invention are particularly suitable for storing and maintaining active pharmaceutical ingredient that needs to be subsequently formulated. In other embodiments, the pharmaceutical containers of the present invention are particularly suitable for storing and maintaining a lyophilized pharmaceutical composition or active pharmaceutical ingredient that requires reconstitution, for example, by addition of saline.

Assaying for Delamination of Pharmaceutical Containers

As noted above, delamination may result in the release of silica-rich glass flakes into a solution contained within the glass container after extended exposure to the solution. Accordingly, the resistance to delamination may be characterized by the number of glass particulates present in a solution contained within the glass container after exposure to the solution under specific conditions. In order to assess the long-term resistance of the glass container to delamination, an accelerated delamination test was utilized. The test consisted of washing the glass container at room temperature for 1 minute and depyrogenating the container at about 320° C. for 1 hour. Thereafter a solution of 20 mM glycine with a pH of 10 in water is placed in the glass container to 80-90% fill, the glass container is closed, and rapidly heated to 100° C. and then heated from 100° C. to 121° C. at a ramp rate of 1 deg/min at a pressure of 2 atmospheres. The glass container and solution are held at this temperature for 60 minutes, cooled to room temperature at a rate of 0.5 deg/min and the heating cycle and hold are repeated. The glass container is then heated to 50° C. and held for two days for elevated temperature conditioning. After heating, the glass container is dropped from a distance of at least 18" onto a firm surface, such as a laminated tile floor, to dislodge any flakes or particles that are weakly adhered to the inner surface of the glass container.

Thereafter, the solution contained in the glass container is analyzed to determine the number of glass particles present per liter of solution. Specifically, the solution from the glass container is directly poured onto the center of a Millipore Isopore Membrane filter (Millipore #ATTP02500 held in an assembly with parts #AP1002500 and #M000025A0) attached to vacuum suction to draw the solution through the filter within 10-15 seconds. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp 153-168. The field of view is set to approximately 1.5 mm×1.5 mm and particles larger than 50 microns are counted manually. There are 9 such measurements made in the center of each filter membrane in a 3×3 pattern with no overlap between images. A minimum of 100 mL of solution is tested. As such, the solution from a plurality of small containers may be pooled to bring the total amount of solution to 100 mL. If the containers contain more than 10 mL of solution, the entire amount of solution from the container is examined for the presence of particles. For containers having a volume greater than 10 mL, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 sets of 10 mL of solution, each of which is analyzed and the particle count averaged over the 10 sets to determine an average particle count. Averaging the particle count over multiple containers accounts for potential variations in the delamination behavior of individual containers. Table 7 summarizes some non-limiting examples of sample volumes and numbers of containers for testing is shown below:

TABLE 7

Table of Exemplary Test Specimens

| Nominal Vial Capacity (mL) | Vial Max Volume (mL) | Minimum Solution per Vial (mL) | Number of Vials in a Trial | Number of Trials | Total solution Tested (mL) |
|---|---|---|---|---|---|
| 2 | 4 | 3.2 | 4 | 10 | 128 |
| 3.5 | 7 | 5.6 | 2 | 10 | 112 |
| 4 | 6 | 4.8 | 3 | 10 | 144 |
| 5 | 10 | 8 | 2 | 10 | 160 |
| 6 | 10 | 8 | 2 | 10 | 160 |
| 8 | 11.5 | 9.2 | 2 | 10 | 184 |
| 10 | 13.5 | 10.8 | 1 | 10 | 108 |

TABLE 7-continued

Table of Exemplary Test Specimens

| Nominal Vial Capacity (mL) | Vial Max Volume (mL) | Minimum Solution per Vial (mL) | Number of Vials in a Trial | Number of Trials | Total solution Tested (mL) |
|---|---|---|---|---|---|
| 20 | 26 | 20.8 | 1 | 10 | 208 |
| 30 | 37.5 | 30 | 1 | 10 | 300 |
| 50 | 63 | 50.4 | 1 | 10 | 504 |

It should be understood that the aforementioned test is used to identify particles which are shed from the interior wall(s) of the glass container due to delamination and not tramp particles present in the container from forming processes or particles which precipitate from the solution enclosed in the glass container as a result of reactions between the solution and the glass. Specifically, delamination particles may be differentiated from tramp glass particles based on the aspect ratio of the particle (i.e., the ratio of the width of the particle to the thickness of the particle). Delamination produces particulate flakes or lamellae which are irregularly shaped and are typically >50 μm in diameter but often >200 μm. The thickness of the flakes is usually greater than about 100 nm and may be as large as about 1 μm. Thus, the minimum aspect ratio of the flakes is typically >50. The aspect ratio may be greater than 100 and sometimes greater than 1000. Particles resulting from delamination processes generally have an aspect ratio which is generally greater than about 50. In contrast, tramp glass particles will generally have a low aspect ratio which is less than about 3. Accordingly, particles resulting from delamination may be differentiated from tramp particles based on aspect ratio during observation with the microscope. Validation results can be accomplished by evaluating the heel region of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101(4), 2012, pages 1378-1384, is noted.

In the embodiments described herein, glass containers which average less than 3 glass particles with a minimum width of 50 μm and an aspect ratio of greater than 50 per trial following accelerated delamination testing are considered "delamination resistant." In the embodiments described herein, glass containers which average less than 2 glass particles with a minimum width of 50 μm and an aspect ratio of greater than 50 per trial following accelerated delamination testing are considered "delamination-stable." In the embodiments described herein, glass containers which average less than 1 glass particle with a minimum width of 50 μm and an aspect ratio of greater than 50 per trial following accelerated delamination testing are considered "delamination-proof." In the embodiments described herein, glass containers which have 0 glass particles with a minimum width of 50 μm and an aspect ratio of greater than 50 per trial following accelerated delamination testing are considered "delamination-free".

Assessing Stability of Pharmaceutical Compositions

As set forth above, any of a variety of active pharmaceutical ingredients can be incorporated within the claimed pharmaceutical container including, for example, a small molecule, a polypeptide mimetic, a biologic, an antisense RNA, a small interfering RNA (siRNA), etc. These active ingredients degrade in varying manners and, thus, assessing the stability thereof in the pharmaceutical containers of the present invention requires different techniques.

Depending on the nature of the active pharmaceutical ingredient, the stability, maintenance and/or continued efficacy of the pharmaceutical compositions contained within the delamination resistant pharmaceutical containers of the present invention can be evaluated as follows.

Biologics API are often susceptible to degradation and/or inactivation arising from various factors, including pH, temperature, temperature cycling, light, humidity, etc. Biologics API are further susceptible to degradation, inactivation or loss, arising from interaction of the pharmaceutical composition with the pharmaceutical container, or delaminants leeching therefrom. For example, biologics may undergo physical degradation which may render the resulting pharmaceutical composition inactive, toxic or insufficient to achieve the desired effect. Alternatively, or in addition, biologics may undergo structural or conformational changes that can alter the activity of the API, with or without degradation. For example, proteins may undergo unfolding which can result in effective loss and inactivity of the API. Alternatively, or in addition, biologics may adhere to the surface of the container, thereby rendering the API administered to the subject insufficient to achieve the desired effect, e.g., therapeutic effect.

(i) General Methods for Investigation of Biologic Compound Degradation

Depending on the size and complexity of the biologic, methods for analysis of degradation of non-biologic, small molecule API may be applied to biologics. For example, peptides and nucleic acids can be analyzed using any of a number of chromatography and spectrometry techniques applicable to small molecules to determine the size of the molecules, either with or without protease or nuclease digestion. However, as proper secondary and tertiary structures are required for the activity of biologics, particularly protein biologics, confirmation of molecular weight is insufficient to confirm activity of biologics. Protein biologics containing complex post-translational modifications, e.g., glycosylation, are less amenable to analysis using chromatography and spectrometry. Moreover, complex biologics, e.g., vaccines which can include complex peptide mixtures, attenuated or killed viruses, or killed cells, are not amenable to analysis by most chromatography or spectrometry methods.

(ii) In Vitro Functional Assays for Investigation of Compound Stability

One or more in vitro assays, optionally in combination with one or more in vivo assays, can be used to assess the stability and activity of the API. Functional assays to determine API stability can be selected based on the structural class of the API and the function of the API. Exemplary assays are provided below to confirm the activity of the API after stability and/or stress testing. It is understood that assays should be performed with the appropriate controls (e.g., vehicle controls, control API not subject to stress or stability testing) with a sufficient number of dilutions and replicate samples to provide data with sufficient statistical significance to detect changes in activity of 10% or less, preferably 5% or less, 4% or less, more preferably 3% or less, 2% or less, or 1% or less, as desired. Such considerations in the art are well understood.

For example, antibody based therapeutics, regardless of the disease or condition to be treated, can be assayed for stability and activity using assays that require specific binding of the antibody to its cognate antigen, e.g., ELISA. The antigen used in the ELISA should have the appropriate conformational structure as would be found in vivo. Antibody based API are used, for example, for the treatment of cancer and inflammatory diseases including autoimmune diseases.

ELISA assays to assay the concentration of a protein biologic API are commercially available from a number of sources, e.g., R&D Systems, BD Biosciences, AbCam, Pierce, Invitrogen.

API are frequently targeted to receptors, particularly cell surface receptors. Receptor binding assays can be used to assess the activity of such agents. API that bind cell surface receptors can be agonists, antagonists or allosteric modulators. API that bind cell surface receptors need not bind the same location as the native ligand to modulate, for example, inhibit or enhance, signaling through the receptor. Depending on the activity of the API, an appropriate assay can be selected, e.g., assay for stimulation of receptor signaling when the API is a receptor agonist; and inhibition assay in which binding of an agonist, e.g., inhibition of activation by a receptor agonist by the API. Such assays can be used regardless of the disease(s) or condition(s) to be treated with the API. Modulation of cellular activity, e.g., cell proliferation, apoptosis, cell migration, modulation of expression of genes or proteins, differentiation, tube formation, etc. is assayed using routine methods. In other assay methods, a reporter construct is used to indicate activation of the receptor. Such methods are routine in the art. APIs that bind to cell surface receptors are used, for example, as anti-cancer agents, anti-diabetic agents, anti-inflammatory agents for the treatment of inflammatory mediated diseases including autoimmune disorders, anti-angiogenic agents, anti-cholinergic agents, bone calcium regulators, muscle and vascular tension regulators, and psychoactive agents.

Modulators of cell proliferation can be assayed for activity using a cell proliferation assays. For example, cell proliferation is induced using anti-anemic agents or stimulators of hematopoietic cell growth. Anti-proliferative agents, e.g., cytotoxic agents, anti-neoplastic agents, chemotherapeutic agents, cytostatic agents, antibiotic agents, are used to inhibit growth of various cell types. Some anti-inflammatory agents also act by inhibiting proliferation of immune cells, e.g., blast cells. In proliferation assays, replicate wells containing the same number of cells are cultured in the presence of the API. The effect of the API is assessed using, for example, microscopy or fluorescence activated cell sorting (FACS) to determine if the number of cells in the sample increased or decreased in response to the presence of the API. It is understood that the cell type selected for the proliferation assay is dependent on the specific API to be tested.

Modulators of angiogenesis can be assayed using cell migration and/or tube formation assays. For cell migration assays, human vascular endothelial cells (HUVECs) are cultured in the presence of the API in transwell devices. Migration of cells through the device at the desired time intervals is assessed. Alternatively, 3-dimensional HUVECs cultures in MATRIGEL can be assessed for tube formation. Anti-angiogenic agents are used, for example, for the treatment of cancer, macular degeneration, and diabetic retinopathy.

Anti-inflammatory API can be assayed for their effects on immune cell stimulation as determined, for example, by modulation of one or more of cytokine expression and secretion, antigen presentation, migration in response to cytokine or chemokine stimulation, and immune cell proliferation. In such assays, immune cells are cultured in the presence of the API and changes in immune cell activity are determined using routine methods in the art, e.g., ELISA and cell imaging and counting.

Anti-diabetic API can be assayed for their effects on insulin signaling, including insulin signaling in response to modulated glucose levels, and insulin secretion. Insulin signaling can be assessed by assessing kinase activation in response to exposure to insulin and/or modulation of glucose levels. Insulin secretion can be assessed by ELISA assay.

Modulators of blood clotting, i.e., fibrinolytics, anti-fibrinolytics, and anti-coagulants, can be assayed for their effects using an INR assay on serum by measuring prothrombin time to determine a prothrombin ratio. Time to formation of a clot is assayed in the presence or absence of the API.

Modulators of muscle or vascular tone can be assayed for their effects using vascular or muscle explants. The tissue can be placed in a caliper for detection of changes in length and/or tension. Whole coronary explants can be used to assess the activity of API on heart. The tissue is contacted with the API, and optionally agents to alter vascular tone (e.g., $K^+$, $Ca^{++}$. The effects of the API on length and/or tension of the vasculature or muscle is assessed.

Psychoactive agents can act by modulation of neurotransmitter release and/or recycling. Neuronal cells can be incubated in the presence of an API and stimulated to release neurotransmitters. Neurotransmitter levels can be assessed in the culture medium collected at defined time points to detect alterations in the level of neurotransmitter present in the media. Neurotransmitters can be detected, for example, using ELISA, LC/MS/MS, or by preloading the vesicles with radioactive neurotransmitters to facilitate detection.

(iii) In Vivo Assays for Investigation of Compound Stability

In addition to in vitro testing for compound stability, API can also be tested in vivo to confirm the stability of the API after storage and/or stress testing. For example, some API are not amenable to testing using in vitro assays due to the complexity of the disease state or the complexity of the response required. For example, psychoactive agents, e.g., antipsychotic agents, anti-depressant agents, nootropic agents, immunosuppressant agents, vasotherapeutic agents, muscular dystrophy agents, central nervous system modulating agents, antispasmodic agents, bone calcium regenerating agents, anti-rheumatic agents, anti-hyperlipidemic agents, hematopoietic proliferation agents, growth factors, vaccine agents, and imaging agents, may not be amenable to full functional characterization using in vitro models. Moreover, for some agents, factors that may not alter in vitro activity may alter activity in vivo, e.g., antibody variable domains may be sufficient to block signaling through a receptor, but the Fc domains may be required for efficacy in the treatment of disease. Further, changes in stability may result in changes in pharmacokinetic properties of an API (e.g., half-life, serum protein binding, tissue distribution, CNS permeability). Finally, changes in stability may result in the generation of toxic degradation or reaction products that would not be detected in vivo. Therefore, confirmation of pharmacokinetic and pharmacodynamic properties and toxicity in vivo is useful in conjunction with stability and stress testing.

(iv) Pharmacokinetic Assays

Pharmacokinetics includes the study of the mechanisms of absorption and distribution of an administered drug, the rate at which a drug action begins and the duration of the effect, the chemical changes of the substance in the body (e.g. by metabolic enzymes such as CYP or UGT enzymes) and the effects and routes of excretion of the metabolites of the drug. Pharmacokinetics is divided into several areas including the extent and rate of absorption, distribution, metabolism and excretion. This is commonly referred to as the ADME scheme:

Absorption—the process of a substance entering the blood circulation.
Distribution—the dispersion or dissemination of substances throughout the fluids and tissues of the body.
Metabolism (or Biotransformation)—the irreversible transformation of parent compounds into daughter metabolites.
Excretion—the removal of the substances from the body. In rare cases, some drugs irreversibly accumulate in body tissue.
Elimination is the result of metabolism and excretion.

Pharmacokinetics describes how the body affects a specific drug after administration. Pharmacokinetic properties of drugs may be affected by elements such as the site of administration and the dose of administered drug, which may affect the absorption rate. Such factors cannot be fully assessed using in vitro models.

The specific pharmacokinetic properties to be assessed for a specific API in stability testing will depend, for example, on the specific API to be tested. In vitro pharmacokinetic assays can include assays of drug metabolism by isolated enzymes or by cells in culture. However, pharmacokinetic analysis typically requires analysis in vivo.

As pharmacokinetics are not concerned with the activity of the drug, but instead with the absorption, distribution, metabolism, and excretion of the drug, assays can be performed in normal subjects, rather than subjects suffering from a disease or condition for which the API is typically administered, by administration of a single dose of the API to the subject. However, if the subject to be treated with the API has a condition that would alter the metabolism or excretion of the API, e.g., liver disease, kidney disease, testing of the API in an appropriate disease model may be useful. Depending on the half life of the compound, samples (e.g., serum, urine, stool) are collected at predetermined time points for at least two, preferably three half-lives of the API, and analyzed for the presence of the API and metabolic products of the API. At the end of the study, organs are harvested and analyzed for the presence of the API and metabolic products of the API. The pharmacokinetic properties of the API subjected to stability and/or stress testing are compared to API not subjected to stability or stress testing and other appropriate controls (e.g., vehicle control). Changes in pharmacokinetic properties as a result of stability and/or stress testing are determined.

(v) Pharmacodynamic Assays

Pharmacodynamics includes the study of the biochemical and physiological effects of drugs on the body or on microorganisms or parasites within or on the body and the mechanisms of drug action and the relationship between drug concentration and effect. Due to the complex nature of many disease states and the actions of many API, the API should be tested in vivo to confirm the desired activity of the agent. Mouse models for a large variety of disease states are known and commercially available (see, e.g., jaxmice.jax.org/query/f?p=205:1:989373419139701::::P1_ADV: 1). A number of induced models of disease are also known. Agents can be tested on the appropriate animal model to demonstrate stability and efficacy of the API on modulating the disease state.

(vi) Specific Immune Response Assay

Vaccines produce complex immune responses that are best assessed in vivo. The specific potency assay for a vaccine depends, at least in part, on the specific vaccine type. The most accurate predictions are based on mathematical modeling of biologically relevant stability-indicating parameters. For complex vaccines, e.g., whole cell vaccines, whole virus vaccines, complex mixtures of antigens, characterization of each component biochemically may be difficult, if not impossible. For example, when using a live, attenuated virus vaccine, the number of plaque forming units (e.g., mumps, measles, rubella, smallpox) or colony forming units (e.g., *S. typhi*, TY21a) are determined to confirm potency after storage. Chemical and physical characterization (e.g., polysaccharide and polysaccharide-protein conjugate vaccines) is performed to confirm the stability and activity of the vaccine. Serological response in animals to inactivated toxins and/or animal protection against challenge (e.g., rabies, anthrax, diphtheria, tetanus) is performed to confirm activity of vaccines of any type, particularly when the activity of the antigen has been inactivated. In vivo testing of vaccines subjected to stability and/or stress testing is performed by administering the vaccine to a subject using the appropriate immunization protocol for the vaccine, and determining the immune response by detection of specific immune cells that respond to stimulation with the antigen or pathogen, detection of antibodies against the antigen or pathogen, or protection in an immune challenge. Such methods are well known in the art. Vaccines include, but are not limited to, meningococcal B vaccine, hepatitis A and B vaccines, human papillomavirus vaccine, influenza vaccine, herpes zoster vaccine, and pneumococcal vaccine.

(vii) Toxicity Assays

Degradation of API can result in the formation of toxic agents. Toxicity assays include the administration of doses, typically far higher than would be used for therapeutic applications, to detect the presence of toxic products in the API. Toxicity assays can be performed in vitro and in vivo and are frequently single, high dose experiments. After administration of the compound, in addition to viability, organs are harvested and analyzed for any indication of toxicity, especially organs involved with clearance of API, e.g., liver, kidneys, and those for which damage could be catastrophic, e.g., heart, brain. The toxicologic properties of the API subjected to stability and/or stress testing are compared to API not subjected to stability or stress testing and other appropriate controls (e.g., vehicle control). Changes in toxicologic properties as a result of stability and/or stress testing are determined.

In accordance with present invention, the degradation, alteration or depletion of API contained within a delamination resistant pharmaceutical container of the present invention can be assessed by a variety of physical techniques. Indeed, in various aspects of the invention, the stability and degradation caused by the interaction of API with the container or delaminants thereof, or changes in concentration or amount of the API in a container can be assessed using techniques as follows. Such methods include, e.g., X-Ray Diffraction (XRPD), Thermal Analysis (such as Differential Scanning calorimetry (DSC), Thermogravimetry (TG) and Hot-Stage Microscopy (HSM), chromatography methods (such as High-Performance Liquid Chromatography (HPLC), Column Chromatography (CC), Gas Chromatography (GC), Thin-Layer Chromatography (TLC), and Super Critical Phase Chromatograph (SFC)), Mass Spectroscopy (MS), Capillary Electrophoresis (CE), Atomic Spectroscopy (AS), vibrational spectroscopy (such as Infrared Spectroscopy (IR)), Luminescence Spectroscopy (LS), and Nuclear Magnetic Resonance Spectroscopy (NMR).

In the case of pharmaceutical formulations where the API is not in solution or needs to be reconstituted into a different medium, XRPD may be a method for analyzing degradation. In ideal cases, every possible crystalline orientation is represented equally in a non-liquid sample.

Powder diffraction data is usually presented as a diffractogram in which the diffracted intensity I is shown as function either of the scattering angle $2\theta$ or as a function of the scattering vector q. The latter variable has the advantage that the diffractogram no longer depends on the value of the wavelength $\lambda$. Relative to other methods of analysis, powder diffraction allows for rapid, non-destructive analysis of multi-component mixtures without the need for extensive sample preparation. Deteriorations of an API may be analyzed using this method, e.g., by comparing the diffraction pattern of the API to a known standard of the API prior to packaging.

Thermal methods of analysis may include, e.g., differential scanning calorimetry (DSC), thermogravimetry (TG), and hot-stage microscopy (HSM). All three methods provide information upon heating the sample. Depending on the information required, heating can be static or dynamic in nature.

Differential scanning calorimetry monitors the energy required to maintain the sample and a reference at the same temperature as they are heated. A plot of heat flow (W/g or J/g) versus temperature is obtained. The area under a DSC peak is directly proportional to the heat absorbed or released and integration of the peak results in the heat of transition.

Thermogravimetry (TG) measures the weight change of a sample as a function of temperature. A total volatile content of the sample is obtained, but no information on the identity of the evolved gas is provided. The evolved gas must be identified by other methods, such as gas chromatography, Karl Fisher titration (specifically to measure water), TG—mass spectroscopy, or TG—infrared spectroscopy. The temperature of the volatilization and the presence of steps in the TG curve can provide information on how tightly water or solvent is held in the lattice. If the temperature of the TG volatilization is similar to an endothermic peak in the DSC, the DSC peak is likely due or partially due to volatilization. It may be necessary to utilize multiple techniques to determine if more than one thermal event is responsible for a given DSC peak.

Hot-Stage Microscopy (HSM) is a technique that supplements DSC and TG. Events observed by DSC and/or TG can be readily characterized by HSM. Melting, gas evolution, and solid—solid transformations can be visualized, providing the most straightforward means of identifying thermal events. Thermal analysis can be used to determine the melting points, recrystallizations, solid-state transformations, decompositions, and volatile contents of pharmaceutical materials.

Other methods to analyze degradation or alteration of API and excipients are infrared (IR) and Raman spectroscopy. These techniques are sensitive to the structure, conformation, and environment of organic compounds. Infrared spectroscopy is based on the conversion of IR radiation into molecular vibrations. For a vibration to be IR-active, it must involve a changing molecular dipole (asymmetric mode). For example, vibration of a dipolar carbonyl group is detectable by IR spectroscopy. Whereas IR has been traditionally used as an aid in structure elucidation, vibrational changes also serve as probes of intermolecular interactions in solid materials.

Raman spectroscopy is based on the inelastic scattering of laser radiation with loss of vibrational energy by a sample. A vibrational mode is Raman active when there is a change in the polarizability during the vibration. Symmetric modes tend to be Raman-active. For example, vibrations about bonds between the same atom, such as in alkynes, can be observed by Raman spectroscopy.

NMR spectroscopy probes atomic environments based on the different resonance frequencies exhibited by nuclei in a strong magnetic field. Many different nuclei are observable by the NMR technique, but those of hydrogen and carbon atoms are most frequently studied. Solid-state NMR measurements are extremely useful for characterizing the crystal forms of pharmaceutical solids. Nuclei that are typically analyzed with this technique include those of 13C, 31P, 15N, 25Mg, and 23Na.

Chromatography is a general term applied to a wide variety of separation techniques based on the sample partitioning between a moving phase, which can be a gas, liquid, or supercritical fluid, and a stationary phase, which may be either a liquid or a solid. Generally, the crux of chromatography lies in the highly selective chemical interactions that occur in both the mobile and stationary phases. For example, depending on the API and the separation required, one or more of absorption, ion-exchange, size-exclusion, bonded phase, reverse, or normal phase stationary phases may be employed.

Mass spectrometry (MS) is an analytical technique that works by ionizing chemical compounds to generate charged molecules or molecule fragments and measuring their mass-to-charge ratios. Based on this analysis method, one can determine, e.g., the isotopic composition of elements in an API and determine the structure of the API by observing its fragmentation pattern.

It would be understood that the foregoing methods do not represent a comprehensive list of means by which one can analyze possible deteriorations, alterations, or concentrations of certain APIs. Therefore, it would be understood that other methods for determining the physical amounts and/or characteristics of an API may be employed. Additional methods may include, but are not limited to, e.g., Capillary Electrophoresis (CE), Atomic Spectroscopy (AS), and Luminescence Spectroscopy (LS).

EXAMPLES

The embodiments of the delamination resistant pharmaceutical containers described herein will be further clarified by the following examples.

Example 1

Six exemplary inventive glass compositions (compositions A-F) were prepared. The specific compositions of each exemplary glass composition are reported below in Table 8. Multiple samples of each exemplary glass composition were produced. One set of samples of each composition was ion exchanged in a molten salt bath of 100% $KNO_3$ at a temperature of 450° C. for at least 5 hours to induce a compressive layer in the surface of the sample. The compressive layer had a surface compressive stress of at least 500 MPa and a depth of layer of at least 45 μm.

The chemical durability of each exemplary glass composition was then determined utilizing the DIN 12116 standard, the ISO 695 standard, and the ISO 720 standard described above. Specifically, non-ion exchanged test samples of each exemplary glass composition were subjected to testing according to one of the DIN 12116 standard, the ISO 695 standard, or the ISO 720 standard to determine the acid resistance, the base resistance or the hydrolytic resistance of the test sample, respectively. The hydrolytic resistance of the ion exchanged samples of each exemplary composition was determined according to the ISO 720 standard. The average results of all samples tested are reported below in Table 8.

As shown in Table 8, exemplary glass compositions A-F all demonstrated a glass mass loss of less than 5 mg/dm² and greater than 1 mg/dm² following testing according to the DIN 12116 standard with exemplary glass composition E having the lowest glass mass loss at 1.2 mg/dm². Accordingly, each of the exemplary glass compositions were classified in at least class S3 of the DIN 12116 standard, with exemplary glass composition E classified in class S2. Based on these test results, it is believed that the acid resistance of the glass samples improves with increased $SiO_2$ content.

Further, exemplary glass compositions A-F all demonstrated a glass mass loss of less than 80 mg/dm² following testing according to the ISO 695 standard with exemplary glass composition A having the lowest glass mass loss at 60 mg/dm². Accordingly, each of the exemplary glass compositions were classified in at least class A2 of the ISO 695 standard, with exemplary glass compositions A, B, D and F classified in class A1. In general, compositions with higher silica content exhibited lower base resistance and compositions with higher alkali/alkaline earth content exhibited greater base resistance.

Table 8 also shows that the non-ion exchanged test samples of exemplary glass compositions A-F all demonstrated a hydrolytic resistance of at least Type HGA2 following testing according to the ISO 720 standard with exemplary glass compositions C-F having a hydrolytic resistance of Type HGA1. The hydrolytic resistance of exemplary glass compositions C-F is believed to be due to higher amounts of $SiO_2$ and the lower amounts of $Na_2O$ in the glass compositions relative to exemplary glass compositions A and B.

Moreover, the ion exchanged test samples of exemplary glass compositions B-F demonstrated lower amounts of extracted $Na_2O$ per gram of glass than the non-ion exchanged test samples of the same exemplary glass compositions following testing according to the ISO 720 standard.

TABLE 8

Composition and Properties of Exemplary Glass Compositions

| | Composition in mole % | | | | | |
|---|---|---|---|---|---|---|
| | A | B | C | D | E | F |
| $SiO_2$ | 70.8 | 72.8 | 74.8 | 76.8 | 76.8 | 77.4 |
| $Al_2O_3$ | 7.5 | 7 | 6.5 | 6 | 6 | 7 |
| $Na_2O$ | 13.7 | 12.7 | 11.7 | 10.7 | 11.6 | 10 |
| $K_2O$ | 1 | 1 | 1 | 1 | 0.1 | 0.1 |
| MgO | 6.3 | 5.8 | 5.3 | 4.8 | 4.8 | 4.8 |
| CaO | 0.5 | 0.5 | 0.5 | 0.5 | 0.5 | 0.5 |
| $SnO_2$ | 0.2 | 0.2 | 0.2 | 0.2 | 0.2 | 0.2 |
| DIN 12116 (mg/dm²) | 3.2 | 2.0 | 1.7 | 1.6 | 1.2 | 1.7 |
| classification | S3 | S3 | S3 | S3 | S2 | S3 |
| ISO 695 (mg/dm²) | 60.7 | 65.4 | 77.9 | 71.5 | 76.5 | 62.4 |
| classification | A1 | A1 | A2 | A1 | A2 | A1 |
| ISO 720 (ug $Na_2O$/g glass) | 100.7 | 87.0 | 54.8 | 57.5 | 50.7 | 37.7 |
| classification | HGA2 | HGA2 | HGA1 | HGA1 | HGA1 | HGA1 |
| ISO 720 (with IX) (ug $Na_2O$/g glass) | 60.3 | 51.9 | 39.0 | 30.1 | 32.9 | 23.3 |
| classification | HGA1 | HGA1 | HGA1 | HGA1 | HGA1 | HGA1 |

Example 2

Three exemplary inventive glass compositions (compositions G-I) and three comparative glass compositions (compositions 1-3) were prepared. The ratio of alkali oxides to alumina (i.e., Y:X) was varied in each of the compositions in order to assess the effect of this ratio on various properties of the resultant glass melt and glass. The specific compositions of each of the exemplary inventive glass compositions and the comparative glass compositions are reported in Table 9. The strain point, anneal point, and softening point of melts formed from each of the glass compositions were determined and are reported in Table 2. In addition, the coefficient of thermal expansion (CTE), density, and stress optic coefficient (SOC) of the resultant glasses were also determined and are reported in Table 9. The hydrolytic resistance of glass samples formed from each exemplary inventive glass composition and each comparative glass composition was determined according to the ISO 720 Standard both before ion exchange and after ion exchange in a molten salt bath of 100% KNO$_3$ at 450° C. for 5 hours. For those samples that were ion exchanged, the compressive stress was determined with a fundamental stress meter (FSM) instrument, with the compressive stress value based on the measured stress optical coefficient (SOC). The FSM instrument couples light into and out of the birefringent glass surface. The measured birefringence is then related to stress through a material constant, the stress-optic or photoelastic coefficient (SOC or PEC) and two parameters are obtained: the maximum surface compressive stress (CS) and the exchanged depth of layer (DOL). The diffusivity of the alkali ions in the glass and the change in stress per square root of time were also determined.

TABLE 9

Glass properties as a function of alkali to alumina ratio

| | Composition Mole % | | | | | |
|---|---|---|---|---|---|---|
| | G | H | I | 1 | 2 | 3 |
| SiO$_2$ | 76.965 | 76.852 | 76.962 | 76.919 | 76.960 | 77.156 |
| Al$_2$O$_3$ | 5.943 | 6.974 | 7.958 | 8.950 | 4.977 | 3.997 |
| Na$_2$O | 11.427 | 10.473 | 9.451 | 8.468 | 12.393 | 13.277 |
| K$_2$O | 0.101 | 0.100 | 0.102 | 0.105 | 0.100 | 0.100 |
| MgO | 4.842 | 4.878 | 4.802 | 4.836 | 4.852 | 4.757 |
| CaO | 0.474 | 0.478 | 0.481 | 0.480 | 0.468 | 0.462 |
| SnO$_2$ | 0.198 | 0.195 | 0.197 | 0.197 | 0.196 | 0.196 |
| Strain (° C.) | 578 | 616 | 654 | 683 | 548 | 518 |
| Anneal (° C.) | 633 | 674 | 716 | 745 | 600 | 567 |
| Softening (° C.) | 892 | 946 | 1003 | 1042 | 846 | 798 |
| Expansion ($10^{-7}$ K$^{-1}$) | 67.3 | 64.3 | 59.3 | 55.1 | 71.8 | 74.6 |
| Density (g/cm$^3$) | 2.388 | 2.384 | 2.381 | 2.382 | 2.392 | 2.396 |
| SOC (nm/mm/Mpa) | 3.127 | 3.181 | 3.195 | 3.232 | 3.066 | 3.038 |
| ISO720 (non-IX) | 88.4 | 60.9 | 47.3 | 38.4 | 117.1 | 208.1 |
| ISO720 (IX450° C.-5 hr) | 25.3 | 26 | 20.5 | 17.8 | 57.5 | 102.5 |
| R$_2$O/Al$_2$O$_3$ | 1.940 | 1.516 | 1.200 | 0.958 | 2.510 | 3.347 |
| CS@t = 0 (MPa) | 708 | 743 | 738 | 655 | 623 | 502 |
| CS/√t (MPa/hr$^{1/2}$) | −35 | −24 | −14 | −7 | −44 | −37 |
| D (μm$^2$/hr) | 52.0 | 53.2 | 50.3 | 45.1 | 51.1 | 52.4 |

The data in Table 9 indicates that the alkali to alumina ratio Y:X influences the melting behavior, hydrolytic resistance, and the compressive stress obtainable through ion exchange strengthening. In particular, FIG. 1 graphically depicts the strain point, anneal point, and softening point as a function of Y:X ratio for the glass compositions of Table 9. FIG. 1 demonstrates that, as the ratio of Y:X decreases below 0.9, the strain point, anneal point, and softening point of the glass rapidly increase. Accordingly, to obtain a glass which is readily meltable and formable, the ratio Y:X should be greater than or equal to 0.9 or even greater than or equal to 1.

Further, the data in Table 2 indicates that the diffusivity of the glass compositions generally decreases with the ratio of Y:X. Accordingly, to achieve glasses can be rapidly ion exchanged in order to reduce process times (and costs) the ratio of Y:X should be greater than or equal to 0.9 or even greater than or equal to 1.

Figure 2:
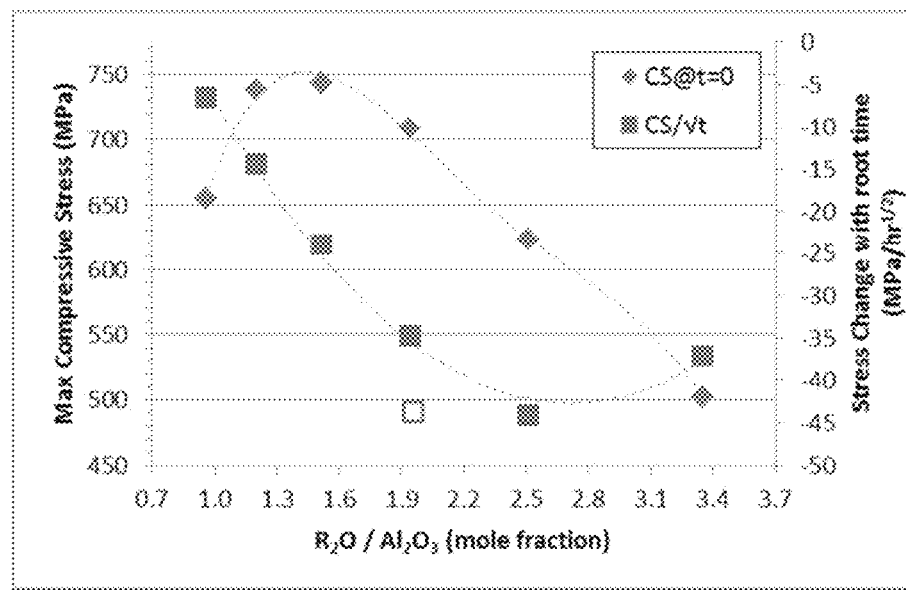
FIG. 2 graphically depicts the relationship between the ratio of alkali oxides to alumina (x-axis) and the maximum compressive stress and stress change (y-axes) of inventive and comparative glass compositions.

Moreover, FIG. 2 indicates that for a given ion exchange time and ion exchange temperature, the maximum compressive stresses are obtained when the ratio of Y:X is greater than or equal to about 0.9, or even greater than or equal to about 1, and less than or equal to about 2, specifically greater than or equal to about 1.3 and less than or equal to about 2.0. Accordingly, the maximum improvement in the load bearing strength of the glass can be obtained when the ratio of Y:X is greater than about 1 and less than or equal to about 2. It is generally understood that the maximum stress achievable by ion exchange will decay with increasing ion-exchange duration as indicated by the stress change rate (i.e., the measured compressive stress divided by the square root of the ion exchange time). FIG. 2 generally shows that the stress change rate decreases as the ratio Y:X decreases.

Figure 3:
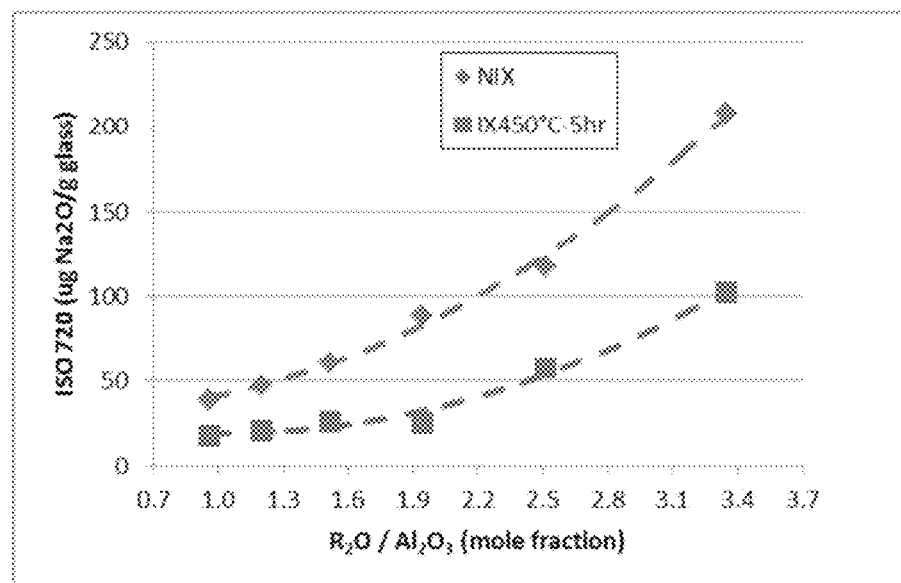
FIG. 3 graphically depicts the relationship between the ratio of alkali oxides to alumina (x-axis) and hydrolytic resistance as determined from the ISO 720 standard (y-axis) of inventive and comparative glass compositions.

FIG. 3 graphically depicts the hydrolytic resistance (y-axis) as a function of the ratio Y:X (x-axis). As shown in FIG. 3, the hydrolytic resistance of the glasses generally improves as the ratio Y:X decreases.

Based on the foregoing it should be understood that glasses with good melt behavior, superior ion exchange performance, and superior hydrolytic resistance can be achieved by maintaining the ratio Y:X in the glass from greater than or equal to about 0.9, or even greater than or equal to about 1, and less than or equal to about 2.

Example 3

Three exemplary inventive glass compositions (compositions J-L) and three comparative glass compositions (compositions 4-6) were prepared. The concentration of MgO and CaO in the glass compositions was varied to produce both MgO-rich compositions (i.e., compositions J-L and 4) and CaO-rich compositions (i.e., compositions 5-6). The relative amounts of MgO and CaO were also varied such that the glass compositions had different values for the ratio (CaO/(CaO+MgO)). The specific compositions of each of the exemplary inventive glass compositions and the comparative glass compositions are reported below in Table 10. The properties of each composition were determined as described above with respect to Example 2.

TABLE 10

Glass properties as function of CaO content

| | Composition Mole % | | | | | |
|---|---|---|---|---|---|---|
| | J | K | L | 4 | 5 | 6 |
| SiO$_2$ | 76.99 | 77.10 | 77.10 | 77.01 | 76.97 | 77.12 |
| Al$_2$O$_3$ | 5.98 | 5.97 | 5.96 | 5.96 | 5.97 | 5.98 |
| Na$_2$O | 11.38 | 11.33 | 11.37 | 11.38 | 11.40 | 11.34 |
| K$_2$O | 0.10 | 0.10 | 0.10 | 0.10 | 0.10 | 0.10 |

TABLE 10-continued

Glass properties as function of CaO content

| | Composition Mole % | | | | | |
|---|---|---|---|---|---|---|
| | J | K | L | 4 | 5 | 6 |
| MgO | 5.23 | 4.79 | 3.78 | 2.83 | 1.84 | 0.09 |
| CaO | 0.07 | 0.45 | 1.45 | 2.46 | 3.47 | 5.12 |
| $SnO_2$ | 0.20 | 0.19 | 0.19 | 0.19 | 0.19 | 0.19 |
| Strain (° C.) | 585 | 579 | 568 | 562 | 566 | 561 |
| Anneal (° C.) | 641 | 634 | 620 | 612 | 611 | 610 |
| Softening (° C.) | 902 | 895 | 872 | 859 | 847 | 834 |
| Expansion ($10^{-7} K^{-1}$) | 67.9 | 67.1 | 68.1 | 68.8 | 69.4 | 70.1 |
| Density ($g/cm^3$) | 2.384 | 2.387 | 2.394 | 2.402 | 2.41 | 2.42 |
| SOC nm/mm/Mpa | 3.12 | 3.08 | 3.04 | 3.06 | 3.04 | 3.01 |
| ISO720 (non-IX) | 83.2 | 83.9 | 86 | 86 | 88.7 | 96.9 |
| ISO720 (IX450° C.-5 hr) | 29.1 | | 28.4 | 33.2 | 37.3 | 40.1 |
| Fraction of RO as CaO | 0.014 | 0.086 | 0.277 | 0.465 | 0.654 | 0.982 |
| CS@t = 0 (MPa) | 707 | 717 | 713 | 689 | 693 | 676 |
| CS/√t ($MPa/hr^{1/2}$) | −36 | −37 | −39 | −38 | −43 | −44 |
| D ($\mu m^2/hr$) | 57.2 | 50.8 | 40.2 | 31.4 | 26.4 | 20.7 |

Figure 4:
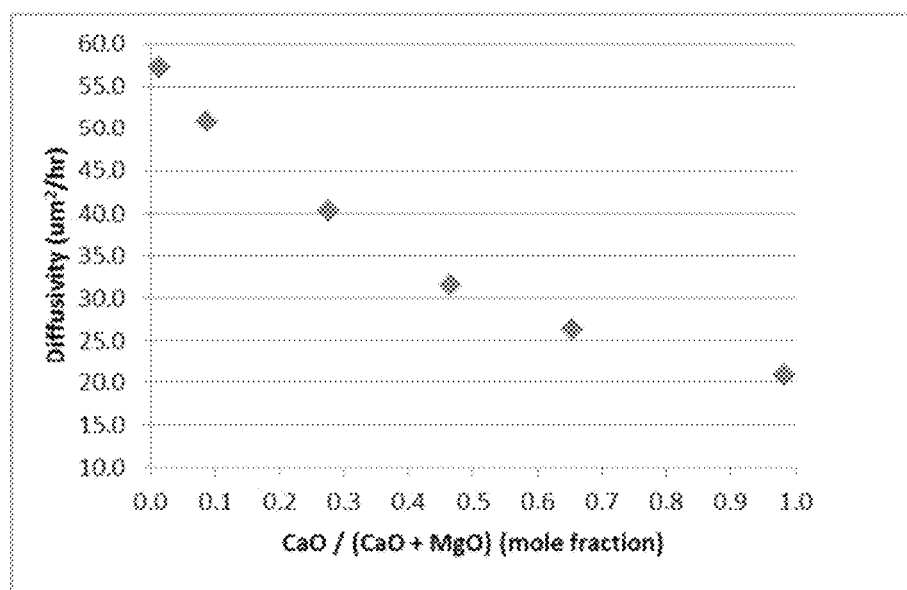
FIG. 4 graphically depicts diffusivity D (y-axis) as a function of the ratio (CaO/(CaO+MgO)) (x-axis) for inventive and comparative glass compositions.
Figure 5:
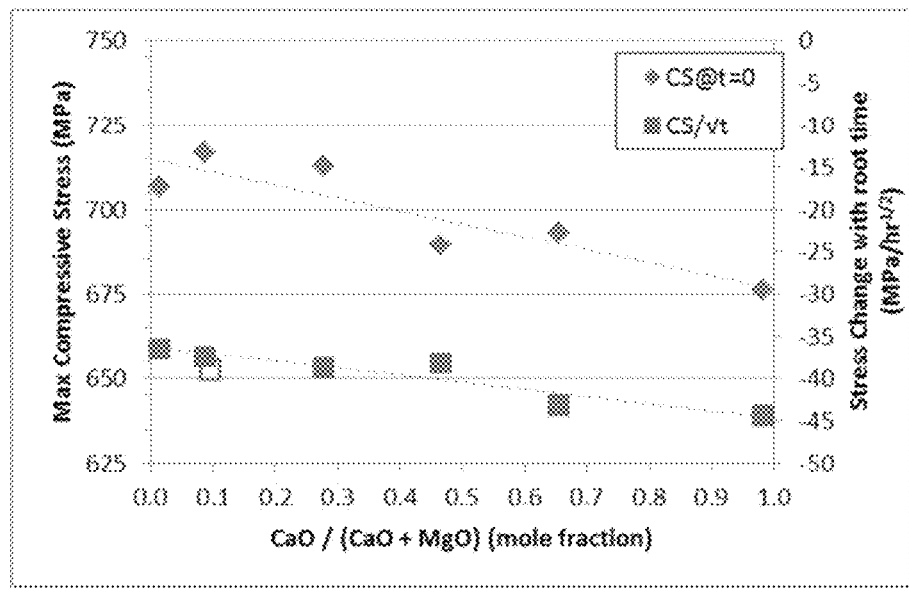
FIG. 5 graphically depicts the maximum compressive stress (y-axis) as a function of the ratio (CaO/(CaO+MgO)) (x-axis) for inventive and comparative glass compositions.

FIG. 4 graphically depicts the diffusivity D of the compositions listed in Table 10 as a function of the ratio (CaO/(CaO+MgO)). Specifically, FIG. 4 indicates that as the ratio (CaO/(CaO+MgO)) increases, the diffusivity of alkali ions in the resultant glass decreases thereby diminishing the ion exchange performance of the glass. This trend is supported by the data in Table 10 and FIG. 5. FIG. 5 graphically depicts the maximum compressive stress and stress change rate (y-axes) as a function of the ratio (CaO/(CaO+MgO)). FIG. 5 indicates that as the ratio (CaO/(CaO+MgO)) increases, the maximum obtainable compressive stress decreases for a given ion exchange temperature and ion exchange time. FIG. 5 also indicates that as the ratio (CaO/(CaO+MgO)) increases, the stress change rate increases (i.e., becomes more negative and less desirable).

Accordingly, based on the data in Table 10 and FIGS. 4 and 5, it should be understood that glasses with higher diffusivities can be produced by minimizing the ratio (CaO/(CaO+MgO)). It has been determined that glasses with suitable diffusivities can be produced when the (CaO/(CaO+MgO)) ratio is less than about 0.5. The diffusivity values of the glass when the (CaO/(CaO+MgO)) ratio is less than about 0.5 decreases the ion exchange process times needed to achieve a given compressive stress and depth of layer. Alternatively, glasses with higher diffusivities due to the ratio (CaO/(CaO+MgO)) may be used to achieve a higher compressive stress and depth of layer for a given ion exchange temperature and ion exchange time.

Moreover, the data in Table 10 also indicates that decreasing the ratio (CaO/(CaO+MgO)) by increasing the MgO concentration generally improves the resistance of the glass to hydrolytic degradation as measured by the ISO 720 standard.

Example 4

Three exemplary inventive glass compositions (compositions M-O) and three comparative glass compositions (compositions 7-9) were prepared. The concentration of $B_2O_3$ in the glass compositions was varied from 0 mol. % to about 4.6 mol. % such that the resultant glasses had different values for the ratio $B_2O_3/(R_2O—Al_2O_3)$. The specific compositions of each of the exemplary inventive glass compositions and the comparative glass compositions are reported below in Table 11. The properties of each glass composition were determined as described above with respect to Examples 2 and 3.

TABLE 11

Glass properties as a function of $B_2O_3$ content

| | Composition Mole % | | | | | |
|---|---|---|---|---|---|---|
| | M | N | O | 7 | 8 | 9 |
| $SiO_2$ | 76.860 | 76.778 | 76.396 | 74.780 | 73.843 | 72.782 |
| $Al_2O_3$ | 5.964 | 5.948 | 5.919 | 5.793 | 5.720 | 5.867 |
| $B_2O_3$ | 0.000 | 0.214 | 0.777 | 2.840 | 4.443 | 4.636 |
| $Na_2O$ | 11.486 | 11.408 | 11.294 | 11.036 | 10.580 | 11.099 |
| $K_2O$ | 0.101 | 0.100 | 0.100 | 0.098 | 0.088 | 0.098 |
| MgO | 4.849 | 4.827 | 4.801 | 4.754 | 4.645 | 4.817 |
| CaO | 0.492 | 0.480 | 0.475 | 0.463 | 0.453 | 0.465 |
| $SnO_2$ | 0.197 | 0.192 | 0.192 | 0.188 | 0.183 | 0.189 |
| Strain (° C.) | 579 | 575 | 572 | 560 | 552 | 548 |
| Anneal (° C.) | 632 | 626 | 622 | 606 | 597 | 590 |
| Softening (° C.) | 889 | 880 | 873 | 836 | 816 | 801 |
| Expansion ($10^{-7} K^{-1}$) | 68.3 | 67.4 | 67.4 | 65.8 | 64.1 | 67.3 |
| Density ($g/cm^3$) | 2.388 | 2.389 | 2.390 | 2.394 | 2.392 | 2.403 |
| SOC (nm/mm/MPa) | 3.13 | 3.12 | 3.13 | 3.17 | 3.21 | 3.18 |
| ISO720 (non-IX) | 86.3 | 78.8 | 68.5 | 64.4 | 52.7 | 54.1 |
| ISO720 (IX450° C.-5 hr) | 32.2 | 30.1 | 26 | 24.7 | 22.6 | 26.7 |
| $B_2O_3/(R_2O—Al_2O_3)$ | 0.000 | 0.038 | 0.142 | 0.532 | 0.898 | 0.870 |
| CS@t = 0 (MPa) | 703 | 714 | 722 | 701 | 686 | 734 |
| CS/√t ($MPa/hr^{1/2}$) | −38 | −38 | −38 | −33 | −32 | −39 |
| D ($\mu m^2/hr$) | 51.7 | 43.8 | 38.6 | 22.9 | 16.6 | 15.6 |

Figure 6:
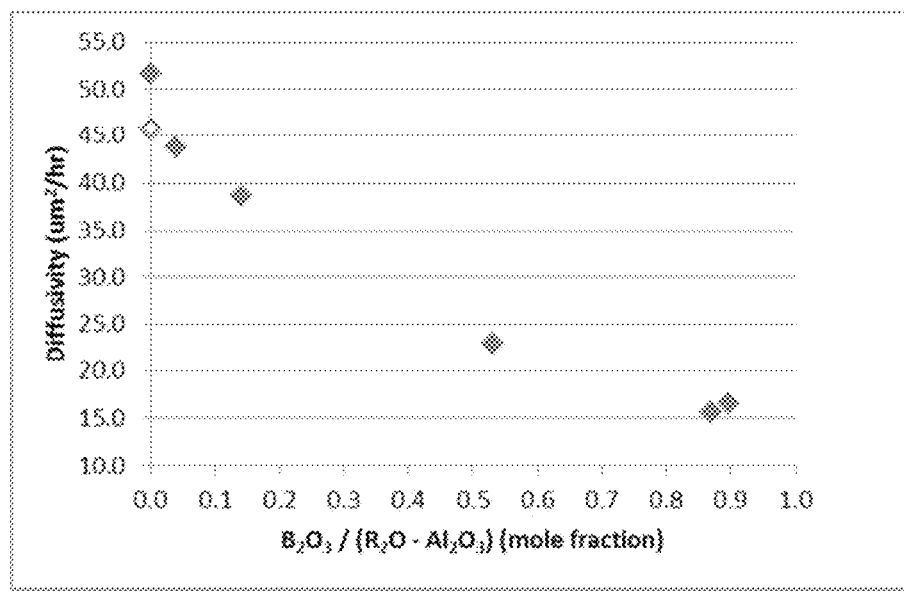
FIG. 6 graphically depicts diffusivity D (y-axis) as a function of the ratio ($B_2O_3$/($R_2O$—$Al_2O_3$)) (x-axis) for inventive and comparative glass compositions.

FIG. 6 graphically depicts the diffusivity D (y-axis) of the glass compositions in Table 11 as a function of the ratio $B_2O_3/(R_2O—Al_2O_3)$ (x-axis) for the glass compositions of Table 11. As shown in FIG. 6, the diffusivity of alkali ions in the glass generally decreases as the ratio $B_2O_3/(R_2O—Al_2O_3)$ increases.

Figure 7:
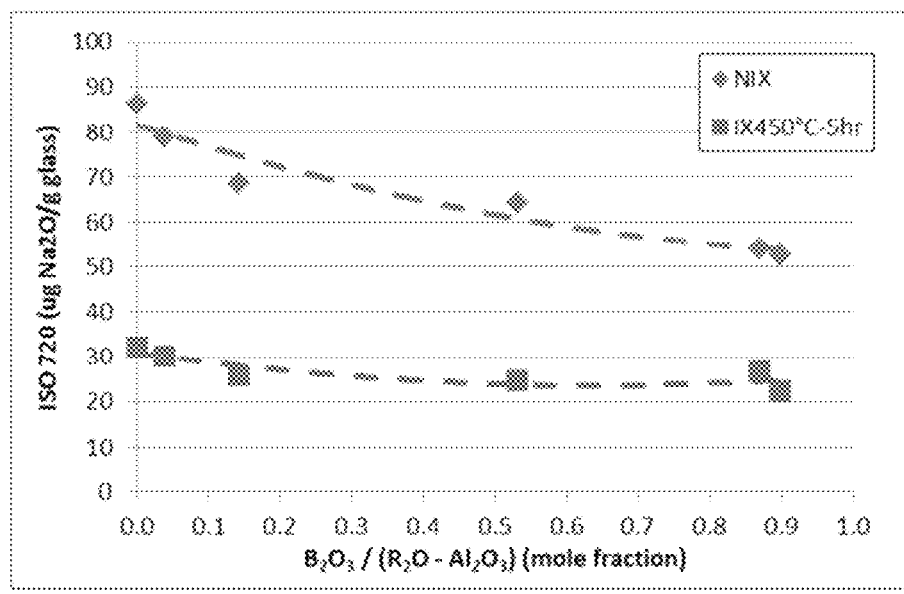
FIG. 7 graphically depicts the hydrolytic resistance as determined from the ISO 720 standard (y-axis) as a function of the ratio ($B_2O_3$/($R_2O$—$Al_2O_3$)) (x-axis) for inventive and comparative glass compositions.

FIG. 7 graphically depicts the hydrolytic resistance according to the ISO 720 standard (y-axis) as a function of the ratio $B_2O_3/(R_2O—Al_2O_3)$ (x-axis) for the glass compositions of Table 11. As shown in FIG. 6, the hydrolytic resistance of the glass compositions generally improves as the ratio $B_2O_3/(R_2O—Al_2O_3)$ increases.

Based on FIGS. 6 and 7, it should be understood that minimizing the ratio $B_2O_3/(R_2O—Al_2O_3)$ improves the diffusivity of alkali ions in the glass thereby improving the ion exchange characteristics of the glass. Further, increasing the ratio $B_2O_3/(R_2O—Al_2O_3)$ also generally improves the resistance of the glass to hydrolytic degradation. In addition, it has been found that the resistance of the glass to degradation in acidic solutions (as measured by the DIN 12116 standard) generally improves with decreasing concentrations of $B_2O_3$. Accordingly, it has been determined that maintaining the ratio $B_2O_3/(R_2O—Al_2O_3)$ to less than or equal to about 0.3 provides the glass with improved hydrolytic and acid resistances as well as providing for improved ion exchange characteristics.

It should now be understood that the glass compositions described herein exhibit chemical durability as well as mechanical durability following ion exchange. These properties make the glass compositions well suited for use in various applications including, without limitation, pharmaceutical packaging materials.

Example 5

Determining the Presence and Amount of Glass Flakes in Pharmaceutical Solutions The resistance to delamination may be characterized by the number of glass particulates present in a pharmaceutical solution contained within a glass container described herein after. In order to assess the long-term resistance of the glass container to delamination, an accelerated delamination test is utilized. The test consists of washing the glass container at room temperature for 1 minute and depyrogenating the container at about 320° C. for 1 hour. Thereafter a pharmaceutical solution is placed in the glass container to 80-90% full, the glass container is closed, and rapidly heated to, for example, 100° C. and then heated from 100° C. to 121° C. at a ramp rate of 1 deg/min at a pressure of 2 atmospheres. The glass container and solution are held at this temperature for 60 minutes, cooled to room temperature at a rate of 0.5 deg./min and the heating cycle and hold are repeated. The glass container is then heated to 50° C. and held for two days for elevated temperature conditioning. After heating, the glass container is dropped from a distance of at least 18" onto a firm surface, such as a laminated tile floor, to dislodge any flakes or particles that are weakly adhered to the inner surface of the glass container.

Thereafter, the pharmaceutical solution contained in the glass container is analyzed to determine the number of glass particles present per liter of solution. Specifically, the solution from the glass container is directly poured onto the center of a Millipore Isopore Membrane filter (Millipore #ATTP02500 held in an assembly with parts #AP1002500 and #M000025A0) attached to vacuum suction to draw the solution through the filter within 10-15 seconds. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp 153-168. The field of view is set to approximately 1.5 mm×1.5 mm and particles larger than 50 microns are counted manually. There are 9 such measurements made in the center of each filter membrane in a 3×3 pattern with no overlap between images. A minimum of 100 mL of solution is tested. As such, the solution from a plurality of small containers may be pooled to bring the total amount of solution to 100 mL. If the containers contain more than 10 mL of solution, the entire amount of solution from the container is examined for the presence of particles. For containers having a volume greater than 10 mL containers, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 sets of 10 mL of solution, each of which is analyzed and the particle count averaged over the 10 sets to determine an average particle count. Averaging the particle count over multiple containers accounts for potential variations in the delamination behavior of individual containers.

It should be understood that the aforementioned test is used to identify particles which are shed from the interior wall(s) of the glass container due to delamination and not tramp particles present in the container from forming processes. Specifically, delamination particles will be differentiated from tramp glass particles based on the aspect ratio of the particle (i.e., the ratio of the width of the particle to the thickness of the particle). Delamination produces particulate flakes or lamellae which are irregularly shaped and are typically>50 µm in diameter but often >200 µm. The thickness of the flakes is usually greater than about 100 nm and may be as large as about 1 µm. Thus, the minimum aspect ratio of the flakes is typically>50. The aspect ratio may be greater than 100 and sometimes greater than 1000. Particles resulting from delamination processes generally have an aspect ratio which is generally greater than about 50. In contrast, tramp glass particles will generally have a low aspect ratio which is less than about 3. Accordingly, particles resulting from delamination may be differentiated from tramp particles based on aspect ratio during observation with the microscope. Validation results can be accomplished by evaluating the heel region of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101(4), 2012, pages 1378-1384, is noted.

Using this method, pharmaceutical compositions can be tested for the presence of glass flakes and various compositions can be compared to each other to assess the safety of various pharmaceutical compositions.

Example 6

Stability Testing of Pharmaceutical Compositions

Stability studies are part of the testing required by the FDA and other regulatory agencies. Stability studies should include testing of those attributes of the API that are susceptible to change during storage and are likely to influence quality, safety, and/or efficacy. The testing should cover, as appropriate, the physical, chemical, biological, and microbiological attributes of the API (e.g., small molecule or biologic therapeutic agent) in the container with the closure to be used for storage of the agent. If the API is formulated as a liquid by the manufacturer, the final formulation should be assayed for stability. If the API is formulated as an agent for reconstitution by the end user using a solution provided by the manufacturer, both the API and the solution for reconstitution are preferably tested for stability as the separate packaged components (e.g., the API subjected to storage reconstituted with solution for reconstitution not subject to storage, API not subject to storage reconstituted with a solution subject to storage, and both API and solution subject to storage). This is particularly the case when the solution for reconstitution includes an active agent (e.g., an adjuvant for reconstitution of a vaccine).

In general, a substance API should be evaluated under storage conditions (with appropriate tolerances) that test its thermal stability and, if applicable, its sensitivity to moisture. The storage conditions and the lengths of studies chosen should be sufficient to cover storage, shipment, and subsequent use.

API should be stored in the container(s) in which the API will be provided to the end user (e.g., vials, ampules, syringes, injectable devices). Stability testing methods provided herein refer to samples being removed from the storage or stress conditions indicated. Removal of a sample preferably refers to removing an entire container from the storage or stress conditions. Removal of a sample should not be understood as withdrawing a portion of the API from the container as removal of a portion of the API from the container would result in changes of fill volume, gas environment, etc. At the time of testing the API subject to stability and/or stress testing, portions of the samples subject to stability and/or stress testing can be used for individual assays.

The long-term testing should cover a minimum of 12 months' duration on at least three primary batches at the time of submission and should be continued for a period of time sufficient to cover the proposed retest period. Additional data accumulated during the assessment period of the registration application should be submitted to the authorities if requested. Data from the accelerated storage condition and, if appropriate, from the intermediate storage condition can be used to evaluate the effect of short-term excursions outside the label storage conditions (such as might occur during shipping).

Long-term, accelerated, and, where appropriate, intermediate storage conditions for API are detailed in the sections below. The general case should apply if the API is not specifically covered by a subsequent section. It is understood that the time points for analysis indicated in the table are suggested end points for analysis. Interim analysis can be preformed at shorter time points (e.g., 1, 2, 3, 4, 5, 6, 7, 8, 9, 10, or 11 months). For API to be labeled as stable for storage for more than 12 months, time points beyond 12 months can be assessed (e.g., 15, 18, 21, 24 months). Alternative storage conditions can be used if justified.

TABLE 12

General Conditions for Stability Analysis

| Study | Storage condition | Time points for analysis |
|---|---|---|
| Long-term | Long-term* 25° C. ± 2° C./60% RH ± 5% RH or 30° C. ± 2° C./65% RH ± 5% RH | 12 months |
| Intermediate | 30° C. ± 2° C./65% RH ± 5% RH | 6 months |
| Accelerated | 40° C. ± 2° C./75% RH ± 5% RH | 6 months |

TABLE 13

Conditions for Stability Analysis for Storage in a Refrigerator

| Study | Storage condition | Minimum time period covered by data at submission |
|---|---|---|
| Long-term | 5° C. ± 3° C. | 12 months |
| Accelerated | 25° C. ± 2° C./60% RH ± 5% RH | 6 months |

TABLE 14

Conditions for Stability Analysis for Storage in a Freezer

| Study | Storage condition | Minimum time period covered by data at submission |
|---|---|---|
| Long-term | −20° C. ± 5° C. | 12 months |

Storage condition for API intended to be stored in a freezer, testing on a single batch at an elevated temperature (e.g., 5° C.±3° C. or 25° C.±2° C.) for an appropriate time period should be conducted to address the effect of short-term excursions outside the proposed label storage condition (e.g., stress during shipping or handling, e.g., increased temperature, multiple freeze-thaw cycles, storage in a non-upright orientation, shaking, etc.).

The assays performed to assess stability of an API include assays to that are used across most APIs to assess the physical properties of the API, e.g., degradation, pH, color, particulate formation, concentration, toxicity, etc. Assays to detect the general properties of the API are also selected based on the chemical class of the agent, e.g., denaturation and aggregation of protein based API. Assays to detect the potency of the API, i.e., the ability of the API to achieve its intended effect as demonstrated by the quantitative measurement of an attribute indicative of the clinical effect as compared to an appropriate control, are selected based on the activity of the particular agent. For example, the biological activity of the API, e.g., enzyme inhibitor activity, cell killing activity, anti-inflammatory activity, coagulation modulating activity, etc., is measured using in vitro and/or in vivo assays such as those provided herein. Pharmacokinetic and toxicological properties of the API are also assessed using methods known in the art, such as those provided herein.

Example 7

Analysis of Adherence to Glass Vials

Changes in the surface of glass can result in changes in the adherence of API to glass. The amount of agent in samples withdrawn from glass vials are tested at intervals to determine if the concentration of the API in solution changes over time. API are incubated in containers as described in the stability testing and/or stress testing methods provided in Example 6. Preferably, the API is incubated both in standard glass vials with appropriate closures and glass vials such as those provided herein. At the desired intervals, samples are removed and assayed to determine the concentration of the API in solution. The concentration of the API is determined using methods and controls appropriate to the API. The concentration of the API is preferably determined in conjunction with at least one assay to confirm that the API, rather than degradation products of the API, is detected. In the case of biologics in which the conformational structure of the biologic agent is essential to its function of the API, the assays for concentration of the biologic are preferably preformed in conjunction with an assay to confirm the structure of the biologic (e.g., activity assay).

For example, in the cases of small molecule APIs, the amount of agent present is determined, for example, by mass spectrometry, optionally in combination with liquid chromatography, as appropriate, to separate the agent from any degradation products that may be present in the sample.

For protein based biologic APIs, the concentration of the API is determined, for example, using ELISA assay. Chromatography methods are used in conjunction with methods to determine protein concentration to confirm that protein fragments or aggregates are not being detected by the ELISA assay.

For nucleic acid biologic APIs, the concentration of the API is determined, for example, using quantitative PCR when the nucleic acids are of sufficient length to permit detection by such methods. Chromatography methods are used to determine both the concentration and size of nucleic acid based API.

For viral vaccine APIs, the concentration of the virus is determined, for example, using colony formation assays.

Example 8

Analysis of Pharmacokinetic Properties

Pharmacokinetics is concerned with the analysis of absorption, distribution, metabolism, and excretion of API. Storage and stress can potentially affect the pharmacokinetic properties of various API. To assess pharmacokinetics of API subject to stability and/or stress testing, agents are incubated in containers as described in Example 6. Preferably, the API are incubated both in standard glass vials with appropriate closures and glass vials such as those provided herein. At the desired intervals, samples are removed and assayed.

The API is delivered to subjects by the typical route of delivery for the API (e.g., injection, oral, topical). As pharmacokinetics are concerned with the absorption and elimination of the API, normal subjects are typically used to assess pharmacokinetic properties of the API. However, if the API is to be used in subjects with compromised ability to absorb or eliminate the API (e.g., subjects with liver or kidney disease), testing in an appropriate disease model may be advantageous. Depending on the half life of the compound, samples (e.g., blood, urine, stool) are collected at predetermined time points (e.g., 0 min, 30 min, 60 min, 90 min, 120 min, 4 hours, 6 hours, 12 hours, 24 hours, 36 hours, 48 hours, etc.) for at least two, preferably three half-lives of the API, and analyzed for the presence of the API and metabolic products of the API. At the end of the study, organs are harvested and analyzed for the presence of the API and metabolic products of the API.

The results are analyzed using an appropriate model selected based on, at least, the route of administration of the API. The pharmacokinetic properties of the API subjected to stability and/or stress testing are compared to API not subjected to stability or stress testing and other appropriate controls (e.g., vehicle control). Changes, if any, in pharmacokinetic properties as a result of storage of the API under each condition are determined.

Example 9

Analysis of Toxicity Profiles

Storage of API can result in alterations of toxicity of API as a result of reactivity of the API with the container, leeching of agents from the container, delamination resulting in particulates in the agent, reaction of the API molecules with each other or components of the storage buffer, or other causes.

Agents are incubated in containers as described in the stability testing and/or stress testing methods provided in Example 6. Preferably, the API is incubated both in standard glass vials with appropriate closures and glass vials such as those provided herein. At the desired intervals, samples are removed and assayed to determine the toxicity the API. The toxicity of the API is determined using methods and controls appropriate to the API. In vitro and in vivo testing can be used alone or in combination to assess changes in toxicity of agents as a result of storage or stress.

In in vitro assays, cell lines are grown in culture and contacted with increasing concentrations of API subjected to stability and/or stress testing for predetermined amounts of time (e.g., 12, 24, 36, 48, and 72 hours). Cell viability is assessed using any of a number of routine or commercially available assays. Cells are observed, for example, by microscopy or using fluorescence activated cell sorting (FACS) analysis using commercially available reagents and kits. For example, membrane-permeant calcein AM is cleaved by esterases in live cells to yield cytoplasmic green fluorescence, and membrane-impermeant ethidium homodimer-1 labels nucleic acids of membrane-compromised cells with red fluorescence. Membrane-permeant SYTO 10 dye labels the nucleic acids of live cells with green fluorescence, and membrane-impermeant DEAD Red dye labels nucleic acids of membrane-compromised cells with red fluorescence. A change in the level of cell viability is detected between the cells contacted with API subjected to stress and/or stability testing in standard glass vials as compared to the glass vials provided herein and appropriate controls (e.g., API not subject to stability testing, vehicle control).

In vivo toxicity assays are performed in animals. Typically preliminary assays are performed on normal subjects. However, if the disease or condition to be treated could alter the susceptibility of the subject to toxic agents (e.g., decreased liver function, decreased kidney function), toxicity testing in an appropriate model of the disease or condition can be advantageous. One or more doses of agents subjected to stability and/or stress testing are administered to animals. Typically, doses are far higher (e.g., 5 times, 10 times) the dose that would be used therapeutically and are selected, at least in part, on the toxicity of the API not subject to stability and/or stress testing. However, for the purpose of assaying stability of API, the agent can be administered at a single dose that is close to (e.g., 70%-90%), but not at, a dose that would be toxic for the API not subject to stability or stress testing. In single dose studies, after administration of the API subject to stress and/or stability testing (e.g., 12 hours, 24 hours, 48 hours, 72 hours), during which time blood, urine, and stool samples may be collected. In long term studies, animals are administered a lower dose, closer to the dose used for therapeutic treatment, and are observed for changes indicating toxicity, e.g., weight loss, loss of appetite, physical changes, or death. In both short and long term studies, organs are harvested and analyzed to determine if the API is toxic. Organs of most interest are those involved in clearance of the API, e.g., liver and kidneys, and those for which toxicity would be most catastrophic, e.g., heart, brain. An analysis is performed to detect a change in toxicity between the API subjected to stress and/or stability testing in standard glass vials as compared to the glass vials provided herein, as compared to API not subject to stability and/or stress testing and vehicle control. Changes, if any, in toxicity properties as a result of storage of the API under each condition are determined.

Example 10

Analysis of Pharmacodynamic Profiles

Pharmacodynamics includes the study of the biochemical and physiological effects of drugs on the body or on microorganisms or parasites within or on the body and the mechanisms of drug action and the relationship between drug concentration and effect. Mouse models for a large variety of disease states are known and commercially available (see, e.g., jaxmice.jax.org/query/f?p=205:1:989373419139701::::P1_ADV:1). A number of induced models of disease are also known.

Agents are incubated in containers as described in the stability testing and/or stress testing methods provided in Example 6. Preferably, the samples are incubated both in standard glass vials with appropriate closures and glass vials such as those provided herein. At the desired intervals, samples are removed and assayed for pharmacodynamic activity using known animal models. Exemplary mouse models for testing the various classes of agents indicated are known in the art.

The mouse is treated with the API subject to stability and/or stress testing. The efficacy of the API subject to stability and/or stress testing to treat the appropriate disease or condition is assayed as compared to API not subject to stability and/or stress testing and vehicle control. Changes, if any, in pharmacodynamic properties as a result of storage of the API under each condition are determined.

Example 11

Confirmation of Stability and Activity of Neupogen® (Filgrastim) and Neulasta® (Pegfilgrastim)

Filgrastim (NEUPOGEN®) is a recombinant human granulocyte colony-stimulating factor (G-CSF). Colony-stimulating factors are glycoproteins which act on hematopoietic cells by binding to specific cell surface receptors and stimulating proliferation, differentiation, commitment, and some end-cell functional activation. Filgrastim is a 175 amino acid protein and has a molecular weight of 18,800 daltons. Filgrastim is a sterile, clear, colorless, preservative-free liquid for parenteral administration containing filgrastim at a specific activity of $1.0 \pm 0.6 \times 10^8$ U/mg (as measured by a cell mitogenesis assay). The product is available in single-use vials and prefilled syringes. The single-use vials contain either 300 mcg or 480 mcg filgrastim at a fill volume of 1.0 mL or 1.6 mL, respectively. The single-use prefilled syringes contain either 300 mcg or 480 mcg filgrastim at a fill volume of 0.5 mL or 0.8 mL, respectively.

Pegfilgrastim (NEULASTA®) is a covalent conjugate of recombinant methionyl human G-CSF (filgrastim) and monomethoxypolyethylene glycol. To produce pegfilgrastim, a 20 kD monomethoxypolyethylene glycol molecule is covalently bound to the N-terminal methionyl residue of filgrastim. The average molecular weight of pegfilgrastim is approximately 39 kD. Pegfilgrastim is supplied in 0.6 mL prefilled syringes for subcutaneous injection. Each syringe contains 6 mg pegfilgrastim (based on protein weight) in a sterile, clear, colorless, preservative-free solution (pH 4.0) containing acetate (0.35 mg), polysorbate 20 (0.02 mg), sodium (0.02 mg), and sorbitol (30 mg) in Water for Injection, USP.

Filgrastim or pegfilgrastim samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The activity of filgrastim or pegfilgrastim is determined using methods and controls appropriate to the agent, e.g., using the methods provided in U.S. Pat. Nos. 5,824,784; 5,582,823; and 5,580,755, each of which is incorporated herein by reference.

Mitogenesis Assay

The G-CSF in vitro bioassay is a mitogenic assay utilizing a G-CSF dependent clone of murine 32D cells. Cells are maintained in Iscoves medium containing 5% FBS and 20 ng/ml rhG-CSF. Prior to sample addition, cells are prepared by rinsing twice with growth medium lacking rhG-CSF. Dilutions of the samples subject or not subject to stability and/or stress testing are prepared for each sample and run in triplicate. Because of their apparent lower activity in vitro, the pegfilgrastim samples are diluted approximately 4-10 times less than the filgrastim samples. A volume of 40 ul of each dilution of sample or standard is added to appropriate wells of a 96 well microtiter plate containing 10,000 cells/well. After forty-eight hours at 37 C and 5.5% $CO_2$. Cell proliferation is assayed. Proliferation of cells treated with filgrastim or pegfilgrastim subject to stability and/or stress testing is compared to cells treated with filgrastim or pegfilgrastim not subject to stress testing and vehicle alone. Changes in cell proliferation, if any, are determined.

Differentiation Assay

Capacity of filgrastim or pegfilgrastim is assayed for the ability to induce differentiation of the murine myelomonocytic leukemic cell line WEHI-3B D+. The cells are assayed in semi-solid agar medium as described in Metcalf, Int. J. Cancer, 25, 225 (1980). The filgrastim or pegfilgrastim subject or not subject to stability and/or stress testing and media controls are incubated with about 60 WEHI-3B D+ cells/well at 37 C. in 5% $CO_2$ in air for 7 days. The samples are incubated in 24 flat bottom well plates and the concentration of filgrastim or pegfilgrastim is varied over an appropriate range. Colonies are classified as undifferentiated, partially differentiated or wholly differentiated and colony cell counts are counted microscopically. The level of differentiation induced by filgrastim or pegfilgrastim subject to stability testing is compared to appropriate controls. Changes in cell differentiation, if any, are determined.

Cell Binding Assays

It was previously reported that WEHI-3B D+ cells and human leukemic cells from newly diagnosed leukemias will bind $^{125}$I-labeled murine G-CSF and that this binding can be competed for by addition of unlabeled G-CSF or human CSF-β. The ability of filgrastim or pegfilgrastim subject or not subject to stability testing to compete for binding of labeled-hpG-CSF to human and murine leukemic cells is tested. The murine or freshly obtained human peripheral blood myeloid leukemic cells are washed three times with PBS/1% BSA. WEHI-3B D+ cells ($5 \times 10^6$) or fresh leukemic cells ($3 \times 10^6$) are incubated in duplicate in PBS/1% BSA (100 ul) in the absence or presence of various concentrations of filgrastim or pegfilgrastim subject to stability testing, and in the presence of labeled-hpG-CSF at 0 C for 90 min. (total volume: 120 ul). Cells are then resuspended and layered over 200 ul ice cold FCS in a 350 ul plastic centrifuge tube and centrifuged (1000 g; 1 min). The pellet is collected by cutting off the end of the tube and pellet and supernatant counted separately, e.g., in a gamma counter (Packard).

Specific binding is determined as total binding in the absence of filgrastim or pegfilgrastim (mean of duplicates) minus binding in the presence of an excess of unlabeled filgrastim or pegfilgrastim (non-specific binding). The level of binding inhibited by filgrastim or pegfilgrastim subject to stability testing is compared to appropriate controls. Changes in competition activity, if any, are determined.

In Vivo Bioassay

Alzet® osmotic pumps are connected to indwelling right jugular vein catheters and implanted subcutaneously in male Syrian golden hamster. Some of the pumps contain filgrastim or pegfilgrastim subject to stability testing, while others contain filgrastim or pegfilgrastim not subject to stability testing, or buffer control. The pumping rate for the osmotic pumps is 1 microliter/hr for up to seven days. Granulocyte, lymphocyte, and erythrocyte counts are monitored. Granulocyte and lymphocyte counts increase in response to treatment with filgrastim or pegfilgrastim, whereas the erythrocyte count is unchanged by buffer treatment. Changes in granulocyte, lymphocyte, and erythrocyte count are compared for filgrastim or pegfilgrastim subject to stability testing and filgrastim or pegfilgrastim not subject to stability testing. Changes in cell count are determined.

Size Exclusion Chromatography-HPLC to Confirm Stability of Pegylation of Pegfilgrastim SEC-HPLC is carried out using a liquid chromatograph, e.g., a Waters HPLC system with a BIOSEP SEC 3000 column, using 100 mM sodium phosphate, pH 6.9, 1 ml/min for 20 minutes. The signal is monitored at 280 nm. An N-terminally monopegylated rh-G-CSF contains a single peak, Lys-35 monopegylated material is a second peak, and Lys-41 monopegylated material is a third peak. This indicates substantial purity among the separated fractions of monopegylated G-CSF.

Example 12

Confirmation of Stability and Activity of Epogen® (Epoetin Alfa)

Epogen® (epoetin alfa) is a 165-amino acid erythropoiesis-stimulating glycoprotein manufactured by recombinant DNA technology. It has a molecular weight of approximately 30,400 daltons. Epoetin alfa is formulated as a sterile, colorless liquid in vials in multiple formulations.

Epoetin alfa samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the activity of the agent in, at least, on in vitro or in vivo assay to assess the biological activity of epoetin alfa. The activity of epoetin alfa is determined using methods and controls appropriate to the agent, for example using methods provided in any one of U.S. Pat. Nos. 5,547,933; 5,756,349; and 5,955,422.

In Vitro Cell Proliferation Assay

A number of erythropoietin-depend cell lines are known in the art. For example, Epo-responsive progenitor cell lines, HCD-57 and Bcl-2-transfected Ba/F3-Epo receptor (Ba/F3-EpoR-Bcl-2), can be used to assess the activity of epoetin alfa (Silva et al., 1999, J. Biol. Chem.). Ba/F3-EpoR-Bcl-2 cells are cultured in the absence of Epo for 20 h and then transfected with a luciferase reporter vector containing a 0.6-kb fragment of the bcl-x promoter (pGL2-0.6R or pGL2-0.6L) and 2.5 mg of the pRL-TK vector (Promega, Madison, Wis.) used to normalize the expression of the luciferase reporter gene. Cells are contacted with epoetin alfa subject to stability and/or stress testing. Cell proliferation is assayed as compared to cells treated with epoetin alfa. Luciferase and kinase activity are measured. Luciferase activity is normalized to kinase activity. Luciferase activity in cells treated with epoetin alfa subjected to or not subjected to stability and/or stress testing and vehicle control. Changes, if any, in luciferase activity are determined.

In Vivo Assay of Epoetin Alfa Activity

Mice are allocated to sample and standard groups in a fully randomized order and identified by a color code for the assay, usually with 8 mice per treatment group. Standard and test samples are diluted to appropriate concentrations with phosphate-buffered saline containing 0.1% bovine serum albumin.

For single injection assays, a single dose of various concentrations of epoetin alfa e.g., 10, 30 or 90 IU EPO of epoetin alfa not subjected to stability or stress testing/0.5 ml per mouse, and an equivalent dilution of the samples subject to stability and/or stress testing, is injected subcutaneously (sc) into the respective animal on day 1. On day 5, a blood sample is taken from the orbital venous sinus of each mouse using a glass capillary tube with the appropriate anticoagulant for the counting method being used.

For multiple injection assays, multiple doses of various concentrations of epoetin alfa, e.g., 1, 3 or 9 IU EPO of epoetin alfa not subjected to stability or stress testing/0.2 ml per mouse per day, and an equivalent dilution of the samples subject to stability and/or stress testing, are injected sc on days 1, 2, 3 and 4 into the respective animal and blood is collected on day 5. Reticulocytes are counted by automated flow cytometry. The number of red blood cells from mice treated with epoetin alfa subjected to or not subjected to stability and/or stress testing and vehicle control are determined Changes, if any, in the stimulation of red blood cell production are determined.

Example 13

Confirmation of Stability and Activity of Enbrel® (Etanercept)

Enbrel® (etanercept) is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. TNF is a naturally occurring cytokine that is involved in normal inflammatory and immune responses. Etanercept is a dimeric soluble form of the p75 TNF receptor that can bind TNF molecules. Etanercept inhibits binding of TNF-α and TNF-β (lymphotoxin alpha [LT-α]) to cell surface TNFRs, rendering TNF biologically inactive. Etanercept is available as a 25 mg or 50 mg prefilled syringe or as a 25 mg multiple use vial.

To determine the stability of etanercept, etanercept samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The stability and/or activity of etanercept is determined using methods and controls appropriate to the agent, for example, using methods provided in U.S. Pat. Nos. 7,915,225; 5,605,690; Re. 36,755.

Effect of Etanercept on Antigen-Induced Arthritis in Rats

Rats immunized with methylated bovine serum albumin (mBSA) in complete Freund's adjuvant develop antigen-induced arthritis (AIA) when challenged with mBSA in knee joints. A similar model of arthritis can also be induced using collagen.

Rats are immunized in the hind flank with 0.5 mg mBSA in complete Freund's adjuvant. Twenty-one days later (day 0), the animals are injected in both hind knee joints with 50 ug mBSA in pyrogen-free saline. Groups of six rats are injected intra-articularly in both knee joints on that day and on the following 2 days with an appropriate dose of etanercept subject to, or not subject to, stability and/or stress testing.

Knee joint width is measured daily on days 0-6 relative to treatment with etanercept subject to, or not subject to, stability and/or stress testing.

Histopathological examination of the joints harvested on day 6 is performed to confirm the degree of swelling. Histopathology scores are derived by evaluating knee joints and scoring their condition as follows: Grade 1, minimal, <10% of area affected; Grade 2, moderate, 10-50% of area affected; Grade 3, marked, at least 50%, but less than all, of area affected; Grade 4, maximal, total area severely affected. A variety of lesions/alterations involving five knee joint structures are evaluated: joint capsule, joint space, synovial membrane, articular cartilage, and subchondral bone. Each structural alteration is scored from 1 to 4, and the scores are added and means are calculated. Histopathology results are expressed as the mean score in each treatment group.

The knee joint width and histopathology scores from rats treated with etanercept subject to. or not subject to, stability and/or stress testing and vehicle control are determined. Changes, if any, in the severity of arthritis are determined.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A delamination resistant pharmaceutical container comprising a pharmaceutical composition stored within the container, wherein the pharmaceutical container comprises a glass composition comprising:
   $SiO_2$ in a concentration greater than about 74 mol. %;
   alkaline earth oxide comprising MgO and CaO, wherein CaO is present in an amount greater than or equal to about 0.1 mol. % and less than or equal to about 1.0 mol. % relative to the glass composition, and a ratio (CaO (mol. %)/(CaO (mol. %)+MgO (mol. %))) is less than or equal to 0.5; and
   Y mol. % alkali oxide, wherein the alkali oxide comprises $Na_2O$ in an amount greater than about 8 mol. %, wherein the glass composition is free of boron and compounds of boron, and
   wherein the pharmaceutical composition comprises one of Filgrastim, Pegfilgrastim, epoetin alfa, etanercept, recombinant human granulocyte-colony stimulating factor or an analog thereof, PEGylated recombinant human granulocyte-colony stimulating factor or an analog thereof, an erythropoiesis-stimulating glycoprotein, or a fusion protein of TNF Receptor 2 and IgG1.

2. The pharmaceutical container of claim 1, wherein the pharmaceutical composition comprises a citrate or phosphate buffer.

3. The pharmaceutical container of claim 2, wherein the buffer is selected from the group consisting of sodium citrate, SSC, monosodium phosphate and disodium phosphate.

4. The pharmaceutical container of claim 1, wherein the pharmaceutical composition is a solution having a pH between about 7 and about 11.

5. The pharmaceutical container of claim 1, wherein the concentration of $SiO_2$ is less than or equal to about 80 mol. %.

6. The pharmaceutical container of claim 1, wherein the glass composition is free from phosphorous and compounds of phosphorous.

7. The pharmaceutical container of claim 1, further comprising X mol. % $Al_2O_3$, wherein a ratio of Y:X is greater than 1.

8. The pharmaceutical container of claim 7, wherein the ratio of Y:X is less than or equal to 2.

9. The pharmaceutical container of claim 7, wherein X is greater than or equal to about 2 mol. % and less than or equal to about 10 mol. %.

10. The pharmaceutical container of claim 7, wherein the alkaline earth oxide is present in an amount from about 3 mol. % to about 13 mol. %.

11. The pharmaceutical container of claim 7, wherein the ratio of Y:X is greater than or equal to 1.3 and less than or equal to 2.

12. The pharmaceutical container of claim 7, wherein X is greater than or equal to about 5 mol. % and less than or equal to about 7 mol. %.

13. The pharmaceutical container of claim 1, wherein the ratio (CaO (mol. %)/(CaO (mol. %)+MgO (mol. %))) is less than or equal to 0.3.

14. The pharmaceutical container of claim 1, further comprising $SnO_2$.

15. A delamination resistant pharmaceutical container comprising a pharmaceutical composition stored within the container, wherein the pharmaceutical container comprises a glass composition comprising:
   from about 74 mol. % to about 78 mol. % $SiO_2$;
   from about 4 mol. % to about 8 mol. % alkaline earth oxide, wherein the alkaline earth oxide comprises both MgO and CaO and a ratio (CaO (mol. %)/(CaO (mol. %)+MgO (mol. %))) is less than or equal to 0.5;
   X mol. % $Al_2O_3$, wherein X is greater than or equal to about 2 mol. % and less than or equal to about 10 mol. %; and
   Y mol. % alkali oxide, wherein the alkali oxide comprises $Na_2O$ in an amount greater than or equal to about 9 mol. % and less than or equal to about 15 mol. %, a ratio of Y:X is greater than 1, and the glass composition is free of boron and compounds of boron, and
   wherein the pharmaceutical composition comprises one of Filgrastim, Pegfilgrastim epoetin alfa, etanercept, recombinant human granulocyte-colony stimulating factor or an analog thereof, PEGylated recombinant human granulocyte-colony stimulating factor or an analog thereof, an erythropoiesis-stimulating glycoprotein, or a fusion protein of TNF Receptor 2 and IgG1.

16. The pharmaceutical container of claim 15, wherein the ratio of Y:X is less than or equal to about 2.

17. The pharmaceutical container of claim 15, wherein the ratio of Y:X is greater than or equal to about 1.3 and less than or equal to about 2.0.

18. The pharmaceutical container of claim 15, wherein the ratio (CaO (mol. %)/(CaO (mol. %)+MgO (mol. %))) is less than or equal to 0.1.

19. The pharmaceutical container of claim 15, wherein the alkaline earth oxide comprises from about 3 mol. % to about 7 mol. % MgO.

20. The pharmaceutical container of claim 15, wherein the alkaline earth oxide comprises CaO in an amount greater than or equal to about 0.1 mol. % and less than or equal to about 1.0 mol. % relative to the glass composition.

21. The pharmaceutical container of claim 15, wherein the alkali oxide further comprises $K_2O$ in an amount greater than or equal to about 0.01 mol. % and less than or equal to about 1.0 mol. %.

22. The pharmaceutical container of claim 15, wherein X is greater than or equal to about 5 mol. % and less than or equal to about 7 mol. %.

23. A delamination resistant pharmaceutical container comprising a pharmaceutical composition stored within the container, wherein the pharmaceutical container comprises a glass composition comprising:
   from about 74 mol. % to about 78 mol. % $SiO_2$;
   alkaline earth oxide comprising both CaO and MgO, wherein the alkaline earth oxide comprises CaO in an amount greater than or equal to about 0.1 mol. % and less than or equal to about 1.0 mol. % relative to the glass composition, and a ratio (CaO (mol. %)/(CaO (mol. %)+MgO (mol. %))) is less than or equal to 0.5;

X mol. % $Al_2O_3$, wherein X is greater than or equal to about 2 mol. % and less than or equal to about 10 mol. %; and Y mol. % alkali oxide, wherein the alkali oxide comprises from about 0.01 mol. % to about 1.0 mol. % $K_2O$ and a ratio of Y:X is greater than 1, and the glass composition is free of boron and compounds of boron, and wherein the pharmaceutical composition comprises one of Filgrastim, Pegfilgrastim, epoetin alfa, etanercept, recombinant human granulocyte-colony stimulating factor or an analog thereof, PEGylated recombinant human granulocyte-colony stimulating factor or an analog thereof, an erythropoiesis-stimulating glycoprotein, or a fusion protein of TNF Receptor 2 and IgG1.

24. The pharmaceutical container of claim 23, wherein the ratio of Y:X is less than or equal to 2.

25. The pharmaceutical container of claim 23, wherein the ratio of Y:X is greater than or equal to 1.3 and less than or equal to 2.0.

26. The pharmaceutical container of claim 23, wherein the ratio (CaO (mol. %)/(CaO (mol. %)+MgO (mol. %))) is less than or equal to 0.1.

27. The pharmaceutical container of claim 23, wherein the glass composition is free of phosphorous and compounds of phosphorous.

28. The pharmaceutical container of claim 23, wherein the alkali oxide further comprises $Na_2O$ in an amount greater than about 8 mol. %.

29. The pharmaceutical container of claim 23, wherein the alkali oxide further comprises $Na_2O$ in an amount greater than or equal to about 2 mol. % and less than or equal to about 15 mol. %.

30. The pharmaceutical container of claim 23, wherein the alkali oxide further comprises from about 9 mol. % to about 13 mol. % $Na_2O$.

31. The pharmaceutical container of claim 23, wherein X is greater than or equal to about 5 mol. % and less than or equal to about 7 mol. %.

32. The pharmaceutical container of claim 1, wherein the pharmaceutical composition comprises Filgrastim.

33. The pharmaceutical container of claim 1, wherein the pharmaceutical composition comprises Pegfilgrastim.

34. The pharmaceutical container of claim 1, wherein the pharmaceutical composition comprises epoetin alfa.

35. The pharmaceutical container of claim 1, wherein the pharmaceutical composition comprises etanercept.

36. The pharmaceutical container of claim 15, wherein the pharmaceutical composition comprises Filgrastim.

37. The pharmaceutical container of claim 15, wherein the pharmaceutical composition comprises Pegfilgrastim.

38. The pharmaceutical container of claim 15, wherein the pharmaceutical composition comprises epoetin alfa.

39. The pharmaceutical container of claim 15, wherein the pharmaceutical composition comprises etanercept.

40. The pharmaceutical container of claim 23, wherein the pharmaceutical composition comprises Filgrastim.

41. The pharmaceutical container of claim 23, wherein the pharmaceutical composition comprises Pegfilgrastim.

42. The pharmaceutical container of claim 23, wherein the pharmaceutical composition comprises epoetin alfa.

43. The pharmaceutical container of claim 23, wherein the pharmaceutical composition comprises etanercept.

* * * * *